(12) United States Patent
Kuusela et al.

(10) Patent No.: US 11,000,697 B2
(45) Date of Patent: *May 11, 2021

(54) INTERACTIVE DOSE MANIPULATION USING PRIORITIZED CONSTRAINTS

(71) Applicant: Varian Medical Systems International AG, Steinhausen (CH)

(72) Inventors: Esa Kuusela, Espoo (FI); Edit Siket-Szasz, Espoo (FI); Marco Lessard, Quebec (CA); Lauri Halko, Helsinki (FI)

(73) Assignee: Varian Medical Systems International AG, Cham (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/563,618

(22) Filed: Sep. 6, 2019

(65) Prior Publication Data

US 2020/0009401 A1    Jan. 9, 2020

Related U.S. Application Data

(63) Continuation of application No. 15/395,521, filed on Dec. 30, 2016, now Pat. No. 10,485,988.

(51) Int. Cl.
*A61N 5/10* (2006.01)
*G21K 1/02* (2006.01)

(52) U.S. Cl.
CPC .......... *A61N 5/103* (2013.01); *A61N 5/1031* (2013.01); *A61N 5/1038* (2013.01); *A61N 5/1077* (2013.01); *G21K 1/025* (2013.01)

(58) Field of Classification Search
CPC .... A61N 5/103; A61N 5/1031; A61N 5/1038; A61N 5/1077; G21K 1/025
See application file for complete search history.

(56) References Cited

U.S. PATENT DOCUMENTS 6,546,073 B1 * 4/2003 Lee ..................... A61N 5/1031
378/65
2006/0256915 A1   11/2006 Otto et al.
(Continued)

FOREIGN PATENT DOCUMENTS

| CH | 709787 | 12/2015 |
| WO | 2005035061 | 4/2005 |
| WO | 2008114159 | 9/2008 |

OTHER PUBLICATIONS

U.S. Appl. No. 15/395,521, "Non Final Office Action", dated Jan. 11, 2019, 14 pages.
(Continued)

*Primary Examiner* — Courtney D Thomas
(74) *Attorney, Agent, or Firm* — Kilpatrick Townsend & Stockton LLP

(57) ABSTRACT

In a method of interactive manipulation of the dose distribution of a radiation treatment plan, after an initial candidate treatment plan has been obtained, a set of clinical goals are transferred into a set of constraints. Each constraint may be expressed in terms of a threshold value for a respective quality index of the dose distribution. The dose distribution can then be modified interactively by modifying the threshold values for the set of constraints. Re-optimization may be performed based on the modified threshold values. A user may assign relative priorities among the set of constraints. When a certain constraint is modified, a re-optimized treatment plan may not violate those constraints that have priorities that are higher than that of the modified constraint, but may violate those constraints that have priorities that are lower than that of the modified constraint.

20 Claims, 18 Drawing Sheets

(56) References Cited

U.S. PATENT DOCUMENTS

2010/0046706 A1    2/2010   Moreau
2010/0054411 A1    3/2010   Nord et al.
2010/0183121 A1    7/2010   Riker et al.

OTHER PUBLICATIONS

International Application No. PCT/EP2017/084629, "International Search Report and Written Opinion", dated Apr. 25, 2018, 13 pages.
U.S. Appl. No. 15/395,521, "Notice of Allowance", dated Jun. 11, 2019, 8 pages.
International Application No. PCT/EP2017/084629, "International Preliminary Report on Patentability", dated Jul. 11, 2019, 9 pages.
Application No. EP20185545.9, Extended European Search Report, dated Sep. 22, 2020, 5 pages.

\* cited by examiner

1300

1302 — Receive a first clinical goal and a second clinical goal, wherein the first clinical goal includes a first acceptable threshold value and a first desired threshold value for a first quality index, and the second clinical goal includes a second acceptable threshold value and a second desired threshold value for a second quality index

1304 — obtain a cost function including a first term with a first weight and a second term with a second weight, wherein the first term is proportional to a value of the first quality index in excess of the first acceptable threshold value, and the second term is proportional to a value of the second quality index in excess of the second acceptable threshold value, and wherein the first weight is inversely proportional to a difference between the first desired threshold value and the first acceptable threshold value, and the second weight is inversely proportional to a difference between the second desired threshold value and the second acceptable threshold value

1306 — Perform optimization using the cost function to obtain an optimal radiation treatment plan having an optimal value for the cost function

*FIG. 13*

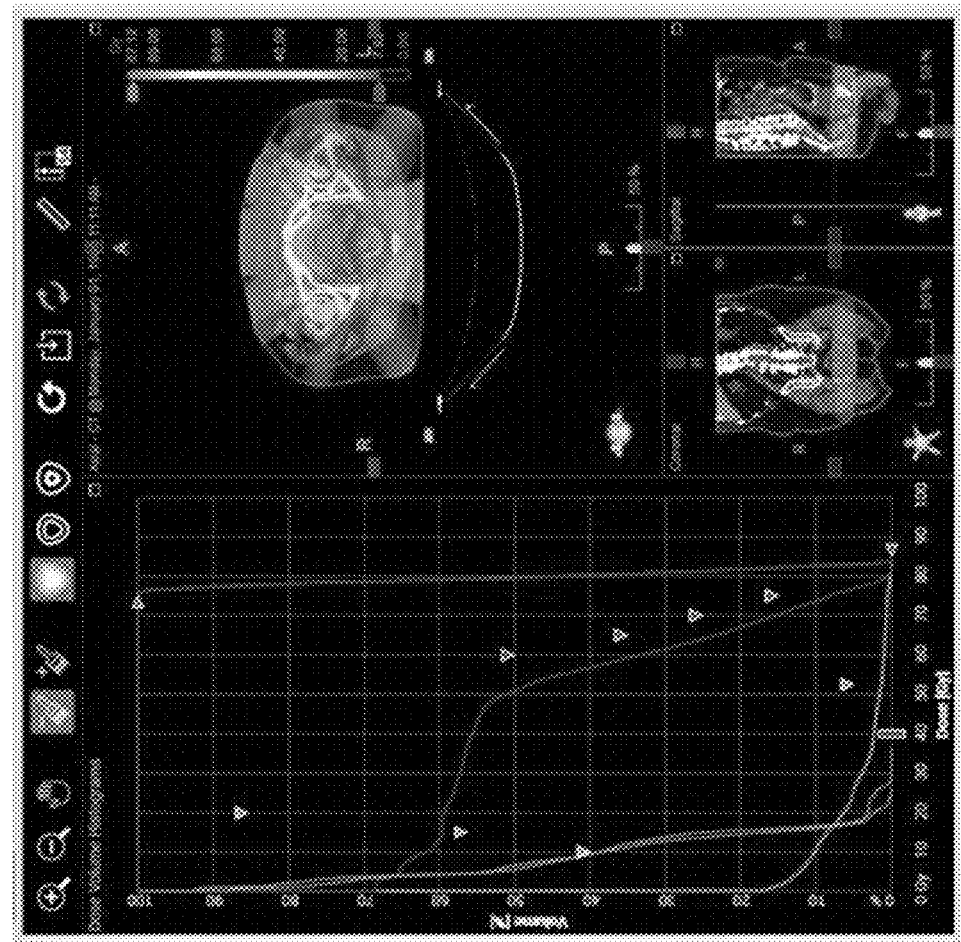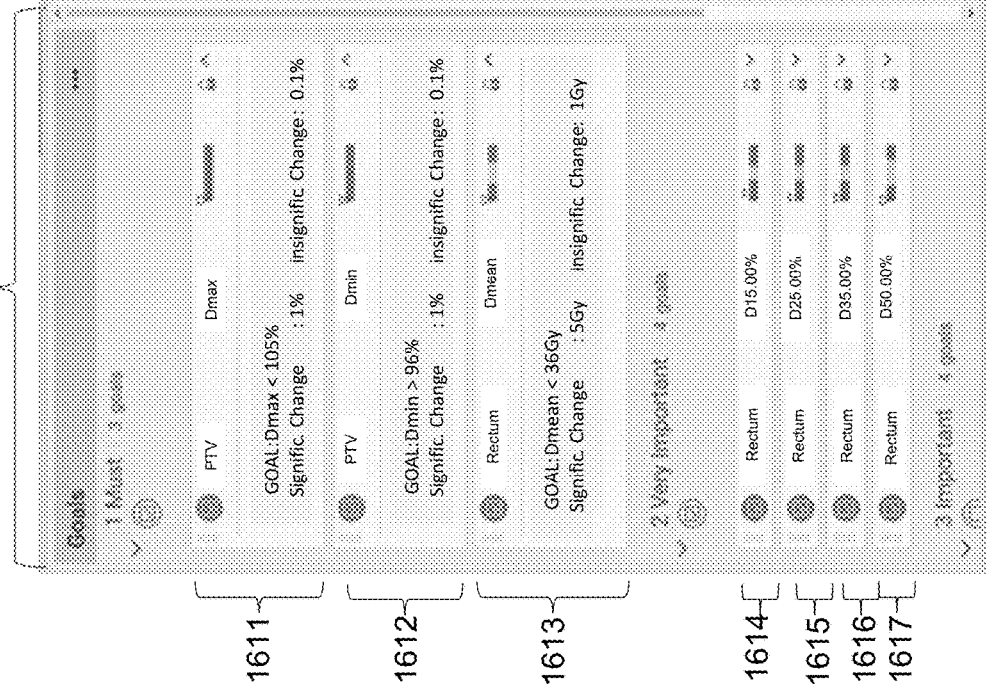
FIG. 16

1700

```
┌─────────────────────────────────────────┐
│ receive a first clinical goal and a second clinical goal,
│ wherein the first clinical goal includes a first threshold
│ value for a first quality index, and the second clinical
│ goal includes a second threshold value for a second
│ quality index
└─────────────────────────────────────────┘  ~1702

┌─────────────────────────────────────────┐
│ receive a first clinically significant change and a first
│ clinically insignificant change for the first quality index,
│ and a second clinically significant change and a second
│ clinically insignificant change for the second quality
│ index
└─────────────────────────────────────────┘  ~1704

┌─────────────────────────────────────────┐
│ Obtain a cost function including a first term, a second
│ term, and a third term, wherein the first term is
│ proportional to a value of the first quality index in excess
│ of the first threshold value and proportional to a value of
│ the second quality index in excess of the second
│ threshold value, the second term relates to the first
│ clinically insignificant change for the first quality index
│ and to the second clinically significant change for the
│ second quality index, and the third term relates to the
│ first clinically significant change for the first quality
│ index and to the second clinically insignificant change
│ for the second quality index
└─────────────────────────────────────────┘  ~1706

┌─────────────────────────────────────────┐
│ Perform optimization using the cost function to obtain an
│ optimal radiation treatment plan having an optimal value
│ for the cost function
└─────────────────────────────────────────┘  ~1708
```

*FIG. 17*

INTERACTIVE DOSE MANIPULATION USING PRIORITIZED CONSTRAINTS

CROSS REFERENCE TO RELATED APPLICATIONS

The present application is a continuation of, and claims the benefit and priority of U.S. application Ser. No. 15/395,521, filed Dec. 30, 2016, now U.S. Pat. No. 10,485,988, issued Nov. 26, 2019, entitled "INTERACTIVE DOSE MANIPULATION USING PRIORITIZED CONSTRAINTS," the entire contents of which are incorporated herein by reference for all purposes.

BACKGROUND

Modern radiation therapy techniques include the use of Intensity Modulated Radiotherapy ("IMRT"), typically by means of an external radiation treatment system, such as a linear accelerator, equipped with a multileaf collimator ("MLC"). Use of multileaf collimators in general, and an IMRT field in particular, allows the radiologist to treat a patient from a given direction of incidence to the target while varying the shape and dose of the radiation beam, thereby providing greatly enhanced ability to deliver radiation to a target within a treatment volume while avoiding excess irradiation of nearby healthy tissue. However, the greater freedom that IMRT and other complex radiotherapy techniques, such as volumetric modulated arc therapy (VMAT), where the system gantry moves while radiation is delivered, and three-dimensional conformal radiotherapy ("3D conformal" or "3DCRT"), afford to radiologists has made the task of developing treatment plans more difficult. As used herein, the term radiotherapy should be broadly construed and is intended to include various techniques used to irradiate a patient, including use of photons (such as high energy x-rays and gamma rays) and particles (such as electron and proton beams). While modern linear accelerators use MLCs, other methods of providing conformal radiation to a target volume are known and are within the scope of the present invention.

Several techniques have been developed to create radiation treatment plans for IMRT or conformal radiation therapy. Generally, these techniques are directed to solving the "inverse" problem of determining the optimal combination of angles, radiation doses and MLC leaf movements to deliver the desired total radiation dose to the target, or possibly multiple targets, while minimizing irradiation of healthy tissue. This inverse problem is even more complex for developing arc therapy plans where the gantry is in motion while irradiating the target volume. Heretofore, radiation oncologists or other medical professionals, such as medical physicists and dosimetrists, have used algorithms to develop and optimize a radiation treatment plan.

Optimization is often used in IMRT to achieve a radiation treatment plan that can fulfill a set of clinical goals in terms of a set of quality indexes. Quality indexes may include statistical quantities of a dose distribution produced by a radiation treatment plan. For example, quality indexes may include maximum dose Dmax for a planned target volume (PTV), minimum dose Dmin for the PTV, mean dose Dmean for an organ at risk (OAR), percentage of the PTV receiving 100% of the prescribed dose V100% (i.e., dose coverage), and the like. Clinical goals may be expressed in terms of a set of threshold values for the set of quality indexes. For example, clinical goals may include the maximum dose Dmax for the PTV should be less than or equal to 105% of the prescribed dose (i.e., $Dmax\_PTV \leq 105\%$), the minimum dose Dmin for the PTV should be greater than or equal to 95% of the prescribed dose (i.e., $Dmin\_PTV \geq 95\%$), the mean dose Dmean to the OAR should be less than 20 Gy (i.e., $Dmean\_OAR \leq 20$ Gy), the percentage of the PTV receiving 100% of the prescribed dose V100% should be greater than 95% (i.e., $V100\% > 95\%$), and the like.

While a physician may be able to recognize a good treatment plan when such a plan has been obtained through optimization, it is difficult to specify a unique set of clinical goals prior to optimization. One possible approach is to use an initial set of clinical goals as a starting point to generate a reasonable candidate plan, and then interactively modify the dose distribution generated by the candidate plan to reach an optimal plan. One way of interactively modifying the plan is to directly make changes to the dose distributions, either in the three-dimensional fluence map or by modifying the dose volume histogram (DVH) curves, for various target structures and critical organs. In this approach, when a final optimal plan is reached, only the resultant dose distribution is recorded, which by itself may not clearly convey the physician's intent when she modified the dose distribution to reach the optimal plan. Therefore, it is desirable to have methods of interactively manipulating dose distribution in a treatment plan where the physician's intent may be preserved.

SUMMARY

According to some embodiments of the present invention, systems, methods, and apparatuses are provided for interactive manipulation of the dose distribution of a radiation treatment plan. For example, after an initial candidate treatment plan has been obtained, a set of clinical goals are transferred into a set of constraints. Each constraint may be expressed in terms of a threshold value for a respective quality index of the dose distribution. The threshold value may be referred to as a "constraint location" for the respective quality index. The dose distribution can then be modified interactively by modifying the constraint locations for the set of constraints. Re-optimization of the treatment plan may be performed based on the modified constraint locations. In this manner, the connection between a clinical goal and a constraint location is maintained. Thus, the physician's final intent is recorded as the changed constraint locations. In some embodiments, a user may assign relative priorities among the set of constraints. According to an embodiment, when a certain constraint is modified, a re-optimized treatment plan may not violate those constraints that have priorities that are higher than that of the modified constraint, but may violate those constraints that have priorities that are lower than that of the modified constraint. In another embodiment, the user may interactively change the relative priorities for one or more constraints. In a further embodiment, two or more constraints may share the same priority. In such cases, when a certain constraint is modified, a re-optimized treatment plan either can or cannot violate other constraints having the same priority.

In other embodiments of the present invention, for cases where two or more clinical goals share the same priority or it is not clear which clinical goal is more important than the other, and the two or more clinical goals cannot be simultaneously met, an optimization algorithm may be designed to seek a solution that minimizes a "distance" to a region where all the clinical goals are met. In one embodiment, a user may specify a first set of threshold values for a set of quality indexes corresponding to the two or more clinical goals, as well as a second set of threshold values for the set of quality indexes. The constraint of the second set of threshold values may be easier to satisfy than the first set of threshold values. For example, the second set of threshold values may represent clinically acceptable threshold values, and the first set of threshold values may represent desired or preferred threshold values. A corresponding difference may be determined for each quality index from the first set of threshold values and the second set of threshold values. An optimal treatment plan may be obtained by optimizing a cost function that includes a plurality of terms (e.g., quadratic terms), where each term relates to a respective quality index, and the weight of each term relates to the difference for the respective quality index.

In yet other embodiments of the present invention, a cost function can take into account both the quality indexes and their derivatives. The optimizer can also support clinical goals where the user has specified preferable trade-offs in advance. For example, the user can specify clinically insignificant changes as well as clinically significant changes for each quality index. In some implementations, the cost function can be generated and dynamically altered during optimization so that any solution achieving clinically significant improvement in one quality index while only deteriorating the other quality index by an insignificant amount may be accepted. In one embodiment, the optimizer may change the constraint location whenever the cost function gradient in a space spanned by the quality indexes has a much greater component with respect to one quality index compared to the other quality index.

Other embodiments are directed to systems and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 13 shows a simplified flowchart illustrating a method of determining an optimal radiation treatment plan according to an embodiment of the present invention.

FIG. 16 illustrates an exemplary user interface that may be used in a method of determining an optimal radiation treatment plan according to an embodiment of the present invention.

FIG. 17 shows a simplified flowchart illustrating a method of determining an optimal radiation treatment plan according to an embodiment of the present invention.

TERMS

Figure 1:
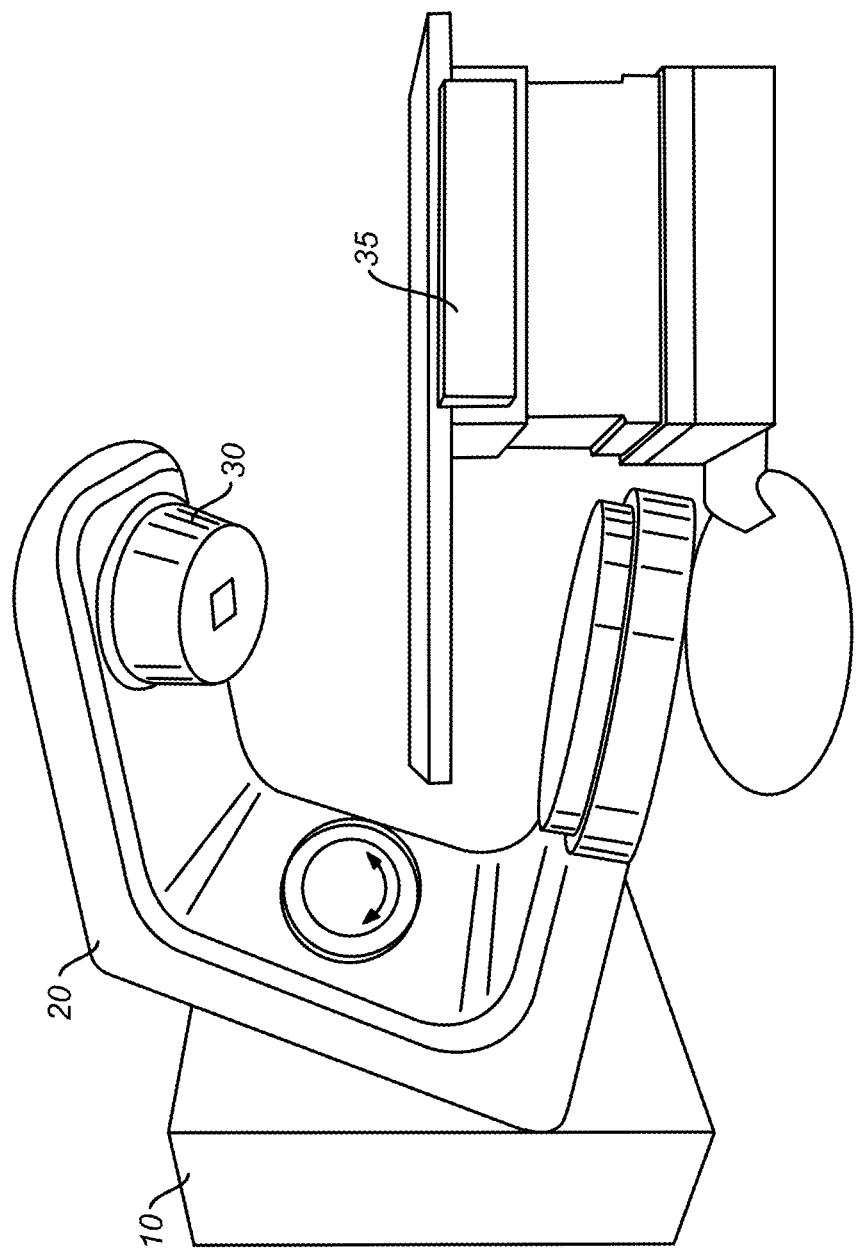
FIG. 1 is a schematic perspective view of a radiation treatment system.

"Radiation" refers to any particles (e.g., photons, electrons, protons etc.) used to treat tissue, e.g., tumors. Examples of radiation include high energy x-rays, gamma rays, electron beams, and proton beams. The different particles can correspond to different types of radiation treatments. The "treatment volume" refers to the entire volume that will be subjected to radiation, and is sometimes referred to as the "irradiated volume." The "target structure", "target volume", and "planning target volume" ("PTV") refer to tissue intended to receive a therapeutic prescribed dose.

A "radiation treatment plan" can include a dose distribution, machine parameters for achieving the dose distribution for a given patient, and information about the given patient. A dose distribution provides information about the variation in the radiation dose with spatial positions within a treatment area of the patient. A "dose distribution" can take many forms, e.g., a dose volume histogram (DVH) or a dose matrix. A DVH can summarize three-dimensional (3D) dose distributions in a graphical 2D format, e.g., where the horizontal axis is the dose (e.g., in units of grays—Gy) absorbed by the target structure (e.g., a tumor) and the vertical axis is the volume percentage. In a differential DVH, the height of a bar at a particular dose indicates the volume of the target structure receiving the particular dose. In a cumulative DVH, the height of a bar at a particular dose represents the volume of the structure receiving greater than or equal to that dose. The cumulative DVH is generally a curve (e.g., when small bin sizes are used), whereas the differential DVH is generally a disjoint bar graph. A drawback of a DVH is that it offers no spatial information; i.e., a DVH does not show where within a structure a dose is received. A dose matrix can provide the dose that each part of the body receives.

DETAILED DESCRIPTION

The present disclosure relates generally to treatment planning for radiation therapy using external-beam radiation treatment systems, and is more particularly directed to interactive dose manipulation using prioritized constraints. For example, after an initial candidate treatment plan has been obtained, a set of clinical goals are transferred into a set of constraints. Each constraint may be expressed in terms of a threshold value for a respective quality index of the dose distribution. The dose distribution can then be modified interactively by modifying the threshold values for the set of constraints. Re-optimization may be performed based on the modified threshold values. Thus, the physician's final intent is recorded as the changed threshold values. In some embodiments, a user may assign relative priorities among the set of constraints. According to an embodiment, when a certain constraint is modified, a re-optimized treatment plan may not violate those constraints that have priorities that are higher than that of the modified constraint, but may violate those constraints that have priorities that are lower than that of the modified constraint.

I. Treatment System

In general, radiation therapy consists of the use of ionizing radiation to treat living tissue, usually tumors. There are many different types of ionizing radiation used in radiation therapy, including high energy x-rays, electron beams, and proton beams. The process of administering the radiation to a patient can be somewhat generalized regardless of the type of radiation used. External beam therapy (EBT), also called external radiation therapy, is a method for delivering a beam or several beams of high-energy x-rays to a patient's tumor. Beams are generated outside the patient (usually by a linear accelerator) and are targeted at the tumor site.

Figure 2:
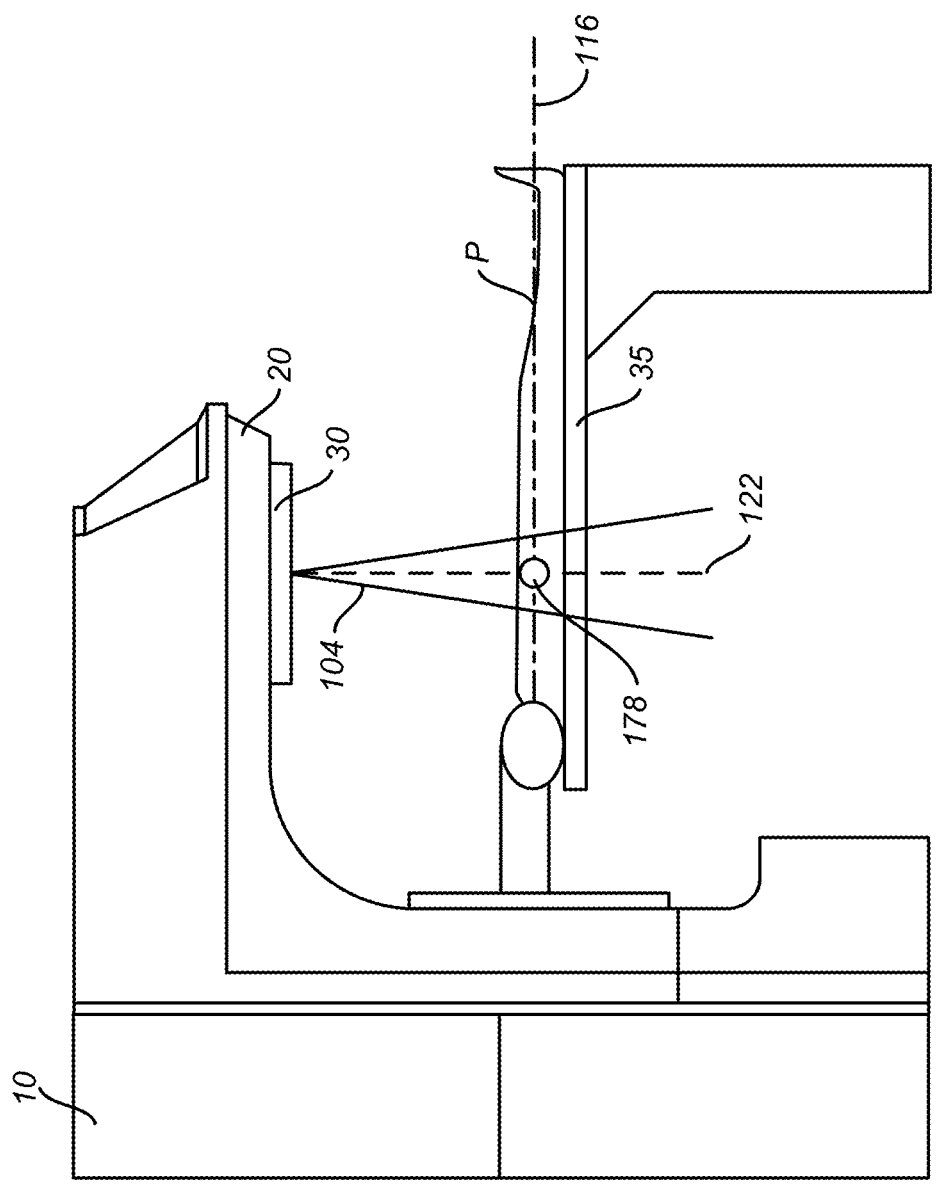
FIG. 2 is a schematic side view of a radiation treatment system.

FIGS. 1 and 2 depict a radiation treatment system of the type that may be used in connection with the present invention. Referring to FIG. 1, a perspective view of radiation treatment system (in this case a linear accelerator) is shown. Typically, such a system is capable of generating either an electron (particle) beam or an x-ray (photon) beam for use in the radiotherapy treatment of patients on a treatment couch 35. Other radiation treatment systems are capable of generating heavy ion particles such as protons. For purposes of the present discussion, only x-ray irradiation will be discussed. However, it will be appreciated by those skilled in the art that the same principles apply to other systems.

Stand 10 supports a rotatable gantry 20 with a treatment head 30. Next to stand 10 there is arranged a control unit (not shown) that includes control circuitry for controlling the different modes of operation of the accelerator. A high voltage source is provided within the stand or in the gantry, to supply voltage to an electron gun (not shown) positioned on an accelerator guide located in the gantry 20. Electrons are emitted from the electron gun into the guide (not shown) where they are accelerated. A source supplies RF (microwave) power for the generation of an electric field within the waveguide. The electrons emitted from the electron gun are accelerated in the waveguide by the electric field, and exit the waveguide as a high energy electron beam, typically at megavoltage energies. The electron beam then strikes a suitable metal target, emitting high energy x-rays in the forward direction.

Referring now to FIG. 2, a somewhat more detailed side view of a radiation treatment system of the type that may be used in connection with the present invention is shown. A patient P is shown lying on the treatment couch 35. X-rays formed as described above are emitted from the target in the treatment head 30 in a divergent beam 104. Typically, a patient plane 116, which is perpendicular to the page in FIG. 2, is positioned about one meter from the x-ray source or target, and the axis of the gantry 20 is located on the plane 116, such that the distance between the target and the isocenter 178 remains constant when the gantry 20 is rotated. The isocenter 178 is at the intersection between the patient plane 116 and the central axis of beam 122. A treatment volume to be irradiated is located about the isocenter 178.

Figure 3:
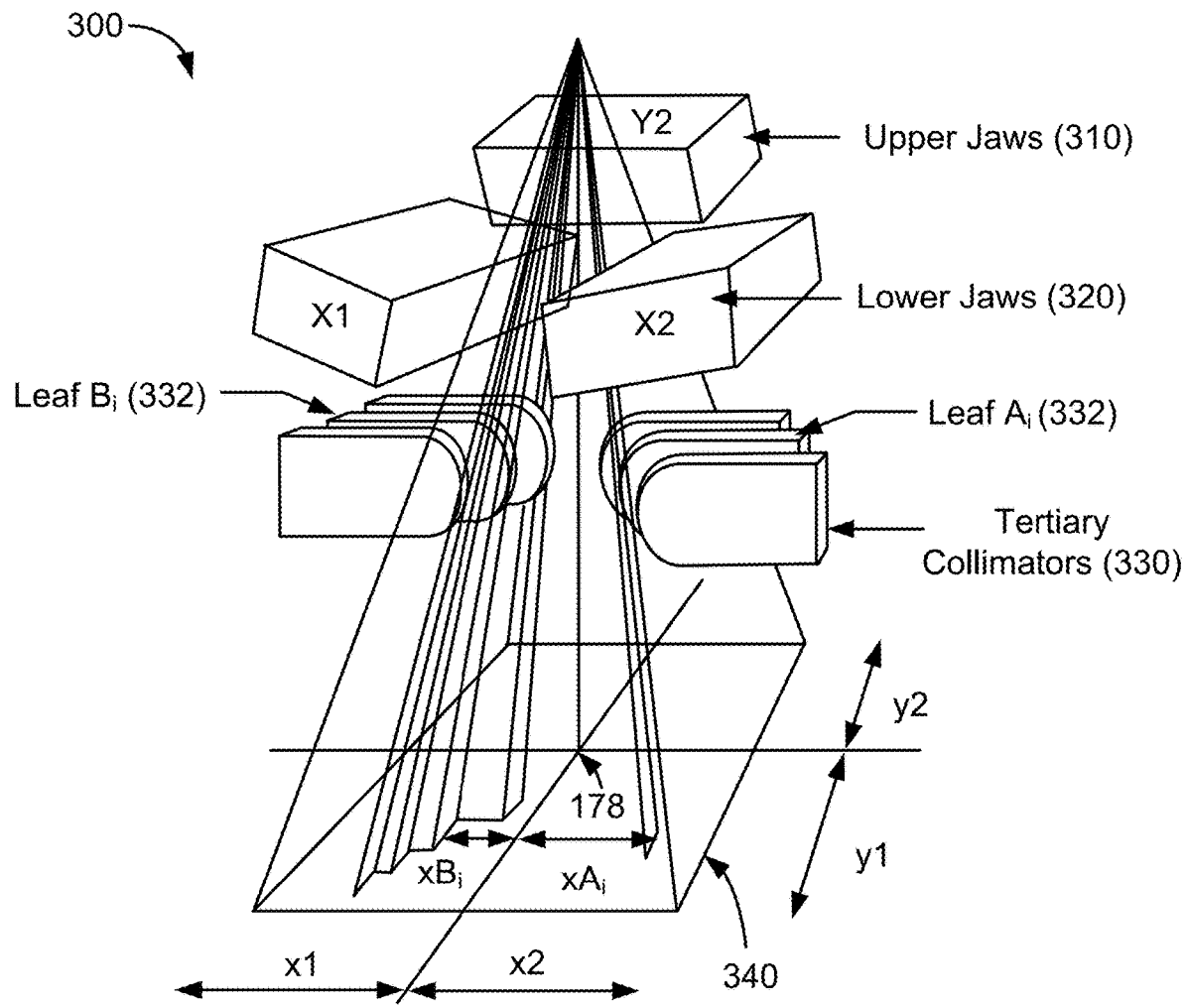
FIG. 3 shows schematically a photon collimation system in a radiation treatment system.

FIG. 3 shows schematically a photon collimation system 300 with upper jaws 310 (i.e., the Y1 and Y2 jaws; the Y1 jaw is omitted for clarity), lower jaws 320 (i.e., the X1 and X2 jaws), and a multileaf collimator (MLC) 330. The field dimensions in the plane 340 at the isocenter 178 are indicated. The upper jaws 310, the lower jaws 320, and the leaves 332 of the MLC 330 comprise an x-ray blocking material, and are positioned in the head 30 to define the width of the x-ray beam at the patient plane. Typically, the jaws 310 and 320 are moveable and, when fully open, define a maximum beam of about 40 cm×40 cm at the patient plane 116. The MLC 330 is positioned at the exit of the head 30, to further shape the x-ray beam. Since its introduction in 1990 the MLC has become a standard feature of most radiation treatment systems. Current MLCs sold by the assignee of the present invention use up to 120 individually controllable leaves, typically thin slices of tungsten, that can be moved into or out of the x-ray beam under the control of system software.

Figure 4:
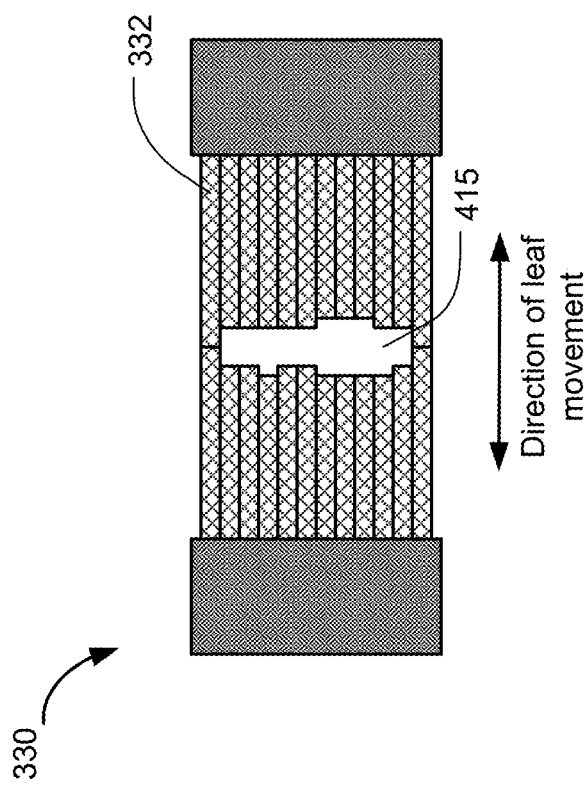
FIG. 4 shows an exemplary multileaf collimator (MLC) plane.

FIG. 4 shows an exemplary MLC plane having a plurality of leaves 332, arranged in opposing pairs, and an aperture 415 created by selected leaf movements. Radiation passes through and is shaped by the aperture 415. Thus, the MLC can be used to collimate the x-rays to provide conformal treatment of tumors from various angles ("3D conformal") as well as intensity modulated radiotherapy ("IMRT"), whereby different radiation doses are delivered to different portions of the treatment area. The treatment volume, i.e., the irradiated volume proximate to the isocenter 178 in the path of the x-ray beam, is defined by the jaws 310 and 320, the leaf sequence of the MLC 330, and the collimator angle, i.e., the angle at which the MLC 330 sits in the head 30. Some external radiation treatment systems may include multiple layers of MLCs. The multiple layers of MLCs may be positioned at different planes and at different collimator angles.

Figure 5:
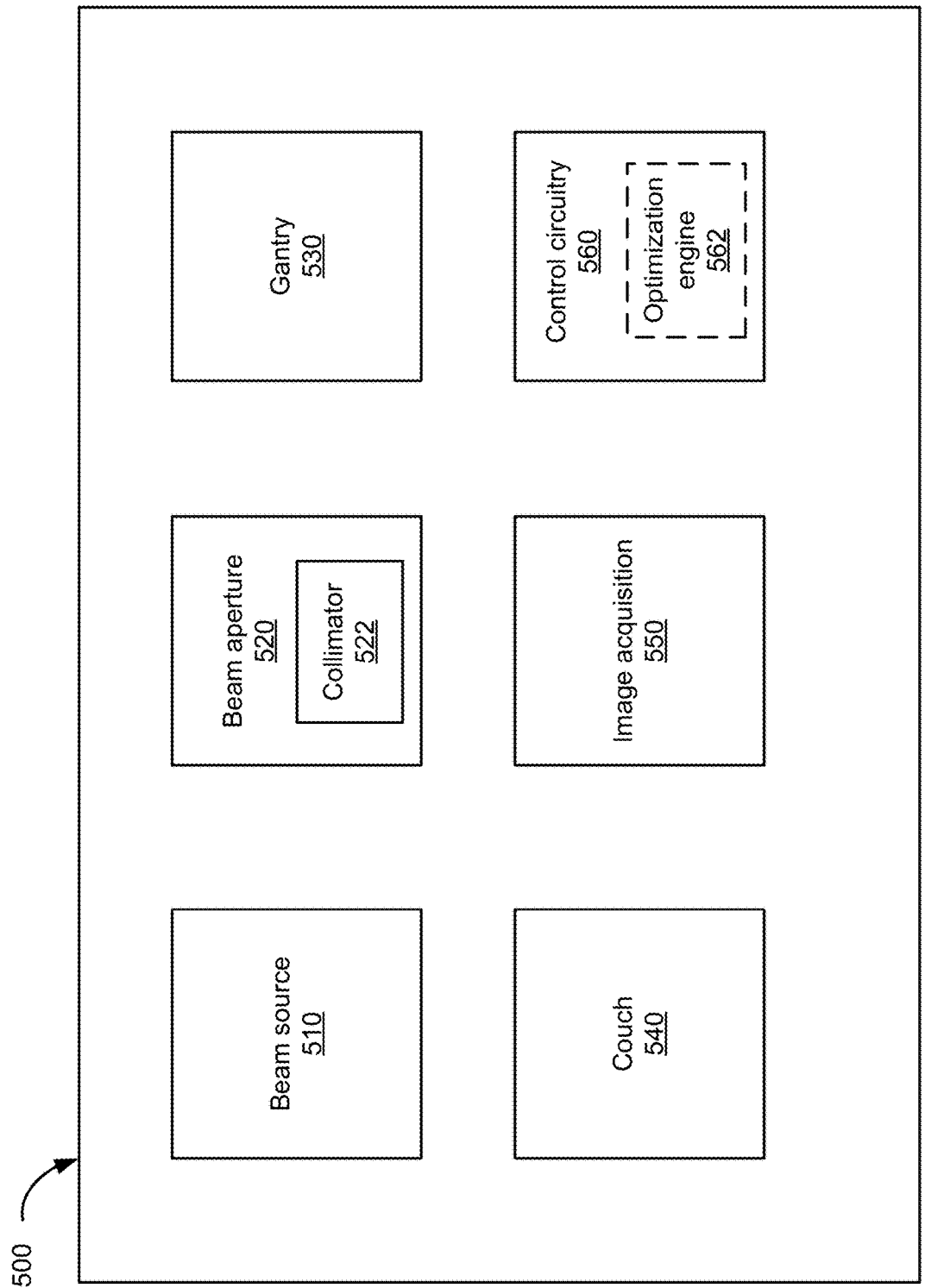
FIG. 5 shows a block diagram of an external-beam radiation treatment system of FIGS. 1 and 2.

FIG. 5 shows a block diagram of an external-beam radiation treatment system 500 of FIGS. 1 and 2. The radiation treatment system 500 includes a beam source 510, a beam aperture 520, a gantry 530, and a couch 540. The beam source 510 is configured to generate a beam of therapeutic radiation. This beam of radiation may include x-rays, particles, and the like. The beam aperture 520 includes an adjustable multi-leave collimator (MLC) 522 for spatially filtering the radiation beam. The couch 540 is configured to support and position a patient. The couch 540 may have six degrees of freedom, namely the translational offsets X, Y, and Z, and the rotation, pitch, and yaw.

The gantry 530 that circles about the couch 540 houses the beam source 510 and the beam aperture 520. The beam source 510 is optionally configured to generate imaging radiation as well as therapeutic radiation. The radiation treatment system 500 may further include an image acquisition system 550 that comprises one or more imaging detectors mounted to the gantry 530.

The radiation treatment system 500 further includes a control circuitry 560 for controlling the operation of the beam source 510, the beam aperture 520, the gantry 530, the couch 540, and the image acquisition system 550. The control circuitry 560 may include hardware, software, and memory for controlling the operation of these various components of the radiation treatment system 500. The control circuitry 560 can comprise a fixed-purpose hard-wired platform or can comprise a partially or wholly-programmable platform. The control circuitry 560 is configured to carry out one or more steps, actions, and other functions described herein. In some embodiments, the control circuitry 560 may include a memory for receiving and storing a radiation treatment plan that defines the control points of one or more treatment fields. The control circuitry 560 may then send control signals to the various components of the radiation treatment system 500, such as the beam source 510, the beam aperture 520, the gantry 530, and the couch 540, to execute the radiation treatment plan. In some embodiments, the control circuitry 560 may include an optimization engine 562 configured for determining a radiation treatment plan. In some other embodiments, the control circuitry 560 may not include an optimization engine. In those cases, a radiation treatment plan may be determined by an optimization engine in a separate computer system, and the radiation treatment plan is then transmitted to the control circuitry 560 of the radiation treatment system 500 for execution.

II. Radiation Treatment Planning

Radiation therapy is generally implemented in accordance with a radiation treatment plan that typically takes into account the desired dose of radiation that is prescribed to be delivered to the tumor, as well as the maximum dose of radiation that can be delivered to surrounding tissue. Various techniques for developing radiation treatment plans may be used. Preferably, the computer system used to develop the radiation treatment plan provides an output that can be used to control the radiation treatment system, including the control points and the MLC leaf movements. Typically, the desired dose prescribed in a radiation treatment plan is delivered over several sessions, called fractions.

Several techniques have been developed to create radiation treatment plans for IMRT or conformal radiation therapy. Generally, these techniques are directed to solving the "inverse" problem of determining the optimal combination of angles, radiation doses and MLC leaf movements to deliver the desired total radiation dose to the target while minimizing irradiation of healthy tissue. This inverse problem is even more complex for developing arc therapy plans, such as volumetric modulated arc therapy (VMAT), where the one or more external treatment coordinates, such as the isocenter location, gantry angle, couch angles, and couch offsets, are in motion while irradiating the target volume. Heretofore, radiation oncologists or other medical professionals, such as medical physicists and dosimetrists, have used one of the available algorithms to develop and optimize a radiation treatment plan.

Typically, such planning starts with volumetric information about the target tumor and about any nearby tissue structures. For example, such information may comprise a map of the planning target volume ("PTV"), such as a prostate tumor, which is prescribed by the physician to receive a certain therapeutic radiation dose with allowable tolerances. Volumetric information about nearby tissues may include for example, maps of the patient's bladder, spinal cord and rectum, each of which may be deemed an organ at risk (OAR) that can only receive a much lower, maximum prescribed amount of radiation without risk of damage. This volumetric information along with the prescribed dose limits and similar objectives set by the medical professionals are the basis for calculating an optimized dose distribution, also referred to as fluence map, which in turn is the basis for determining a radiation treatment plan. The volumetric information may, for example, be reduced to an objective function or a single figure of merit that accounts for the relative importance of various trade-offs inherent in a radiation treatment plan, along with constraints that must be met for the radiation treatment plan to be medically acceptable or physically possible.

Treatment planning algorithms can account for the capabilities of the specific radiation treatment system they are used with, for example, the energy spectrum and intensity profile of the radiation beam, and the capabilities of the MLC. Generally speaking, treatment planning algorithms proceed by calculating the radiation dose received by each voxel in the treatment volume, adjusting one or more variable system parameters, such as the angle of irradiation or the positions of the MLC leaves, and then recalculating the dose received by each voxel. This process is ideally performed iteratively until an optimized plan is reached. However, the amount of time needed to perform the large number of calculations for each iteration places a practical limit on the number of iterations that can be performed. Accordingly, the algorithm is terminated after a predetermined amount of time, after a predetermined number of iterations, or after some other practical limit is reached. Generally speaking, there is a trade-off between the accuracy and speed of the different algorithms available for treatment planning.

III. Interactive Dose Manipulation Using Prioritized Constraints

Optimization is often used in IMRT to achieve a radiation treatment plan that can fulfill a set of clinical goals in terms of a set of quality indexes. While a physician may be able to recognize a good treatment plan when such a plan has been obtained through optimization, it might be difficult to specify a unique set of clinical goals prior to optimization. One possible approach may be to construct a cost function using an initial set of reference values for a set of quality indexes (the initial set of reference values are usually not the same as clinically acceptable threshold values but may be related to them), and perform optimization using the cost function to generate a reasonable candidate treatment plan. The candidate treatment plan produces an initial dose distribution. A user may then interactively modify the candidate plan by directly make changes to the initial dose distributions, either in the three-dimensional dose distribution or by modifying the dose volume histogram (DVH) curves, for various target structures and critical organs. In this approach, when a final optimal plan is reached, only the resultant dose distribution is recorded, which by itself may not clearly convey the physician's intent when she modified the dose distribution to reach the optimal plan. For example, it may not be clear whether the physician was trying to decrease the mean dose to an organ at risk (OAR), or to increase the percentage of the target volume (PTV) receiving 100% of the prescribed dose, when she modified the dose distribution. Thus, it may not be clear how the physician's intent could be transferred to a different field arrangement, a different fractionation scheme, or a modified patient anatomy. Another way of interactively modifying the plan may be to modify the initial set of clinical goals and then re-optimize the plan with the modified goals. This approach, however, may not allow direct study of trade-offs between different clinical goals. For example, a physician may wish to explore how much a quality index related to one clinical goal can be improved without deteriorating another quality index related to another clinical goal by more than a clinically significant amount.

According to an embodiment of the present invention, in a method of interactive manipulation of the dose distribution of a radiation treatment plan, after an initial candidate treatment plan has been obtained, a set of clinical goals are transferred into a set of constraints, which are used for interactive re-optimization. In mathematical optimization, constraint optimization is the process of optimizing an objective function with respect to some variables in the presence of constraints on those variables. The objective function is either a cost function or energy function which is to be minimized, or a reward function or utility function, which is to be maximized. Constraints can be either hard constraints which set conditions for the variables that are required to be satisfied, or soft constraints which have some variable values that are penalized in the objective function if, and based on the extent that, the conditions on the variables are not satisfied.

According to some embodiments, each constraint may be expressed in terms of a threshold value for a respective quality index of the dose distribution. The threshold value may be referred to as a "constraint location" for the respective quality index. The dose distribution can then be modified interactively by modifying the constraint locations for the set of constraints. In this manner, the connection between a clinical goal and a constraint location is maintained. Thus, the physician's final intent is recorded as the changed constraint locations.

In some embodiments, a user may assign relative priorities among the set of constraints. According to an embodiment, when a certain constraint is modified, in the re-optimization, any constraint having a priority that is higher than that of the modified constraint are forced to be met, while any constraint having a priority that is lower than that of the modified constraint is allowed be violated. In another embodiment, the user may interactively change the relative priorities for one or more constraints. In a further embodiment, two or more constraints may share the same priority. In such cases, when a certain constraint is modified, in the re-optimization, other constraints having the same priority are either forced to be met or are allowed to be violated.

A. Example User Interface for Interactive Dose Manipulation

Figure 6:
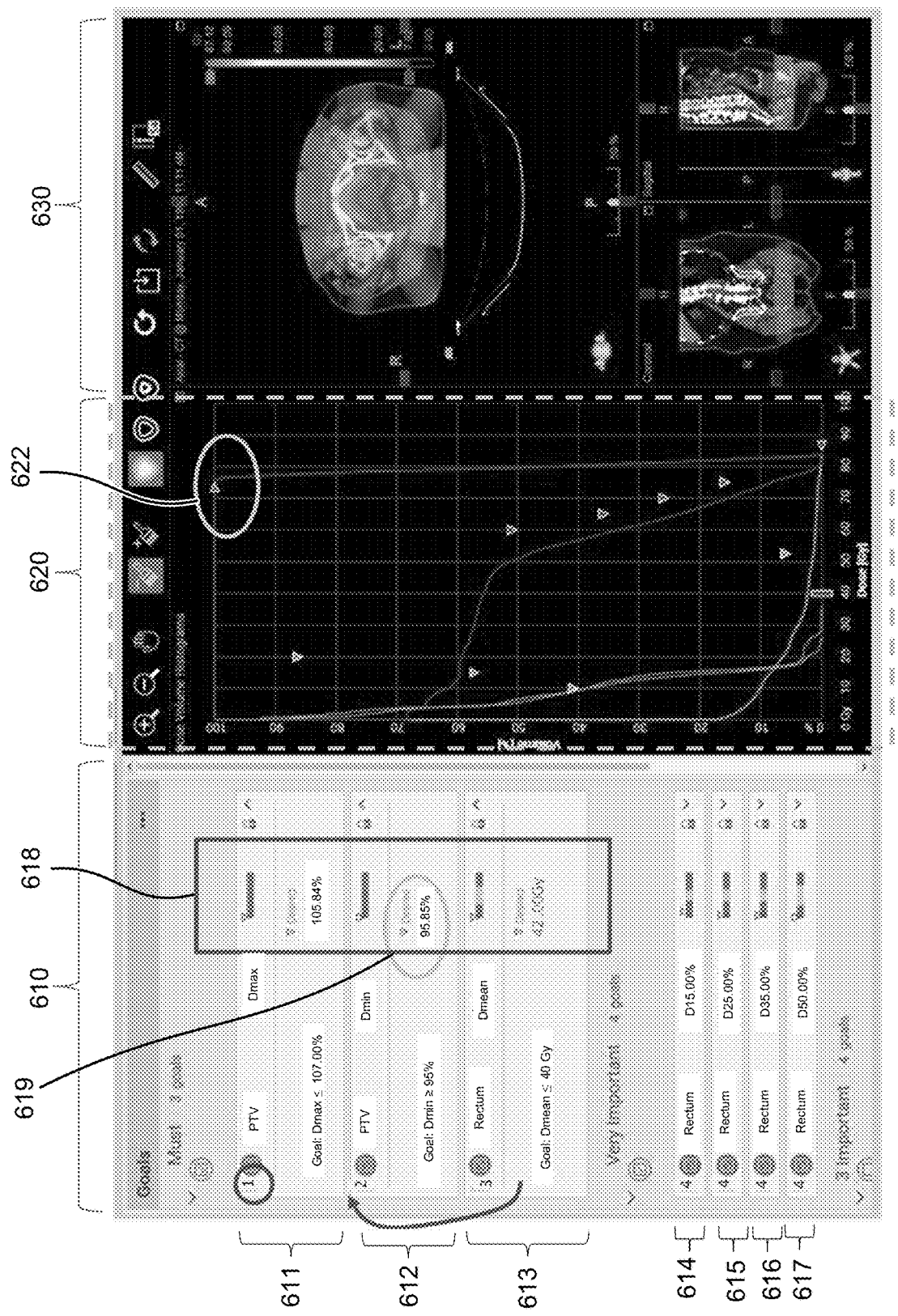
FIG. 6 illustrates an exemplary user interface that may allow a user to interactively manipulate the dose distribution of a radiation treatment plan according to an embodiment of the present invention.

FIG. 6 illustrates an exemplary user interface that may allow a user to interactively manipulate the dose distribution of a radiation treatment plan according to an embodiment of the present invention. The section 620 in the middle of the user interface displays DVH curves for various optimization structures (e.g., the PTV, an OAR, and the like) that correspond to the initial dose distribution of the initial treatment plan that was determined using a set of initial set of reference values for a set of quality indexes. The section 630 on the right side of the user interface displays some two-dimensional slices of the three-dimensional dose distribution of the initial treatment plan.

The section 610 on the left side of the user interface includes a plurality of fields 611-617. Each field corresponds to a clinical goal in terms of a respective quality index. For instance, in the example shown in FIG. 6, the first field 611 corresponds to the maximum dose Dmax for the planned target volume (PTV); the second field 612 corresponds to the minimum dose Dmin for the PTV; the third field 613 corresponds to the mean dose Dmean for an organ at risk (OAR) (e.g., the rectum); and the fields 614-617 correspond to various clinical goals relating to the dose to an OAR. Each field may include an initial threshold value for the corresponding treatment goal. For example, in the field 611, the initial threshold value for Dmax for the PTV is indicated as "Goal: Dmax≤107.00%."

The display area 618 in the section 610 allows the user to enter new threshold values (i.e., change the "constraint locations") for the set of quality indexes. For example, in the field 612, the user may enter 95.85% as the new threshold value (i.e., the "desired" value) for Dmin to the PTV. The user can edit the number 619 in the display area 618. Alternatively, the user can make a change in the corresponding DVH graph in the middle section 620 of the user interface by dragging a handle 622 on the DVH graph to a desired location. For example, the user can drag the handle 622 of the DVH graph of an OAR to a lower dosage value. As the DVH graph is modified, the "desired" threshold value for the corresponding quality index may be updated accordingly in the display area 618.

B. Re-Optimization and Prioritizing Constraints

After the user has changed a threshold value for one of the clinical goals as discussed above, the system may re-optimize the treatment plan in order to meet the new threshold value for that clinical goal. Since the initial treatment plan is typically an optimized solution that is fully determined by multiple constraints, changing a single constraint may not result in a solution that can also meet all other constraints. In other words, a re-optimized treatment plan may have to violate one or more other constraints in order to meet the modified constraint. According to an embodiment of the present invention, the set of constraints are prioritized. For instance, in the example illustrated in FIG. 6, the constraint Dmax for the PTV is given the highest priority (i.e., having the priority of "1"); the constraint Dmin for the PTV is given the second highest priority (i.e., having the priority of "2"); the constraint Dmean for the OAR is given the third highest priority (i.e., having the priority of "3"); and the other constraints are given the shared fourth highest priority (i.e., having the priority of "4").

When a certain constraint is modified, a re-optimized treatment plan is not allowed to violate any constraint having a priority that is higher than that of the modified constraint, and is allowed to violate any constraint having a priority that is lower than that of the modified constraint. For instance, assume that a user changes the constraint location of Dmin for the PTV from 95.00% to 95.85%, as indicated by the circle 619 in the display area 618. Because the constraint regarding Dmax for the PTV has a priority (priority of "1") that is higher than that of the constraint being modified (priority of "2"), a re-optimized treatment plan cannot violate the constraint regarding Dmax for the PTV (e.g., the value of Dmax for the PTV cannot be greater than 107.00%). On the other hand, because the constraint regarding Dmean for the OAR has a priority (priority of "3") that is lower than that of the constraint being modified, the re-optimized treatment plan may violate the constraint regarding Dmean for the OAR (e.g., the value of Dmean for the OAR is allowed to go above 40.00 Gy). After re-optimization, the system may update the threshold values of lower priority constraints with achievable values. For instance, assuming that the lowest value achievable for Dmean for the OAR is 42.00 Gy after re-optimization, the system may update the threshold value of Dmean for the OAR to 42.00 Gy.

In some embodiments, the user may choose to start with the constraint with the highest priority, and then proceed to the constraint with the next highest priority, and so on until all the constraints have been handled. In some embodiments, after handling a constraint with a lower priority, the user may wish to go back to a constraint with a higher priority. In this manner, the user can study the trade-offs among the various clinical goals until she finds an optimal achievable treatment plan.

The method of interactive manipulation of the dose distribution according to embodiments of the present invention may afford several advantages as compared to conventional approaches. For example, in the manner described above, the connection between a clinical goal and a constraint location is maintained and the physician's intent is recorded as the changed threshold value for the constraint. In contrast, in an approach where changes are made directly to the dose distribution, only the resultant dose distribution is recorded, which may not clearly convey the physician's intent, and consequently it may not be clear how the physician's intent could be transferred to a different field arrangement, a different fractionation scheme, or a modified patient anatomy. In addition, in the manner described above, the physician can directly study the trade-offs among various clinical goals, which may not be as transparent in an approach where a modified set of clinical goals are used to re-optimize the treatment plan.

C. Constraints Having Same Priority and Other Options

In some cases, it may be difficult to determine the relative priorities among two or more clinical goals. Some embodiments can be generalized to cases where more than one clinical goal has the same priority. For example, when one constraint is modified, other constraints that have the same priority as that of the modified constraint, as well as those constraints with higher priorities, are forced to be met in the re-optimization; and only those constraints with lower priorities are allowed be violated. In another example, when one constraint is modified, other constraints that have the same priority as that of the modified constraint, as well as those constraints with lower priorities, are allowed to be violated in the re-optimization. In yet another example, a user may select whether or not other constraints having the same priority as that of the modified constraint are allowed to be violated in the re-optimization.

Other user options and user actions may be possible. In one embodiment, the user may select that the constraint with the closest higher priority is also allowed to be violated in the re-optimization. In another embodiment, the user may be allowed to change the relative priorities of some of the clinical goals (e.g., as illustrated by the arrow 624 in FIG. 6). In yet another embodiment, instead of assigning priorities to the clinical goals, the user may select which constraints are allowed to be violated and which ones are forced to be met, so that she can study trade-offs among the various clinical goals. In a further embodiment, the user can create a new clinical goal as a new constraint, and the system may perform re-optimization including the newly added clinical goal.

D. Modification of Optimization Structure

According to another embodiment, to allow a user to alter the three-dimensional dose distribution directly (so-called "painting dose"), the user can change the shape of an optimization structure, such as the contour of a PTV or an OAR. An interactive user action can be similar to using a brush tool in a painting application where the user is provided a "brush" with which she can change the shape of an optimization structure (thus this method may be referred to as "painting structure"). For example, if the user thinks that radiation dose should be delivered to a larger volume than the current volume of the PTV, the user can enlarge the contour of the PTV to enlarge its volume. The system may re-optimize the radiation treatment plan according to the enlarged PTV.

Figure 7:
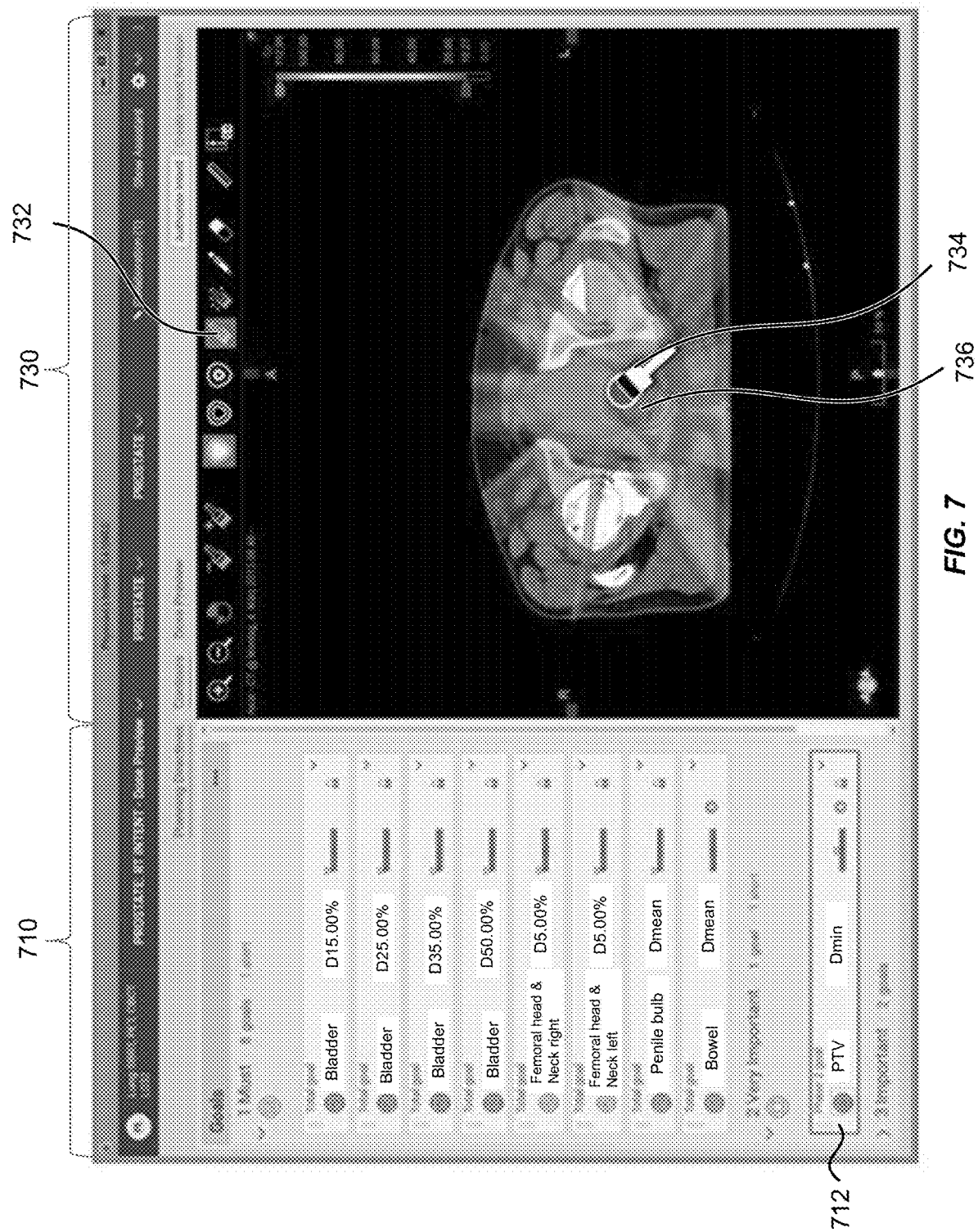
FIG. 7 illustrates an exemplary user interface that can allow a user to interactively manipulate the dose distribution of a radiation treatment plan by changing the shape of an optimization structure, according to an embodiment of the present invention.

FIG. 7 illustrates an exemplary user interface that can allow a user to interactively manipulate the dose distribution of a radiation treatment plan by changing the shape of an optimization structure, according to an embodiment of the present invention. The section 710 on the left side of the user interface includes a plurality of fields, each field corresponds to a clinical goal with respect to an optimization structure. For example, the field 712 corresponds to dose coverage of the PTV (i.e., percentage of the PTV receiving 100% of the prescribed dose).

The section 730 on the right side of the user interface displays a two-dimensional slice of the three-dimensional dose distribution. If the user thinks that radiation dose should be delivered to a larger volume than the current volume of the PTV, she may select the field 712 in the section 710 that corresponds to dose coverage to the PTV. In response to the selection of field 712, the contour 736 of the PTV would become active in the dose distribution image in the section 730 of the user interface. For example, the contour 736 of the PTV may be depicted in red color, as illustrated in FIG. 7. The user may then select the brush tool icon 732 on the top of the section 730. The cursor would then be changed into a "brush" 734. The user can use the brush to make contour 736 of the PTV larger by painting it larger. In one embodiment, the system may re-optimize the radiation treatment plan according to the enlarged PTV.

E. Alternative Embodiment

According to another embodiment, a method of interactive manipulation of the dose distribution of a radiation treatment plan may be described as follows. First, an initial set of candidate treatment plans are generated by selecting all treatment plans that can be realized with the selected patient geometry and field geometry restrictions. Next, a set of clinical goals are converted into a set of constraints. The set of constraints are ranked with relative priorities in an order of importance.

According to an embodiment, a physician may start with modifying the constraint having the highest priority, and check if there exists a subset of the candidate treatment plans satisfying the modified constraint that is non-empty. If the subset is non-empty, that clinical goal is marked as met and the initial set of candidate treatment plans is replaced by the subset. If the subset is empty (i.e., none of the treatment plans in the initial set can meet the modified constraint), that clinical goal is marked as not met. In one embodiment, the initial set of candidate treatment plans is kept unchanged. In another embodiment, the initial set of candidate treatment plans is replaced with a subset where the quality index value associated to that clinical goal reaches a value that is as close to clinically acceptable value as possible. In one embodiment, the constraint location for that clinical goal may be updated to the location that is achievable. The physician may then proceed to handle the constraint of the next highest priority. This process may be repeated until all constraints have been handled.

According to an embodiment, once all clinical goals have been handled, a final optimal treatment plan may be selected from the final subset of treatment plans. In some embodiments, the final optimal treatment plan may be obtained by optimizing an appropriate cost function. For example, the cost function may be designed to minimize the amount of violation of the most important un-met constraint. Alternatively, the cost function may be designed to leave as much margin as possible for the most important fulfilled constraint. Other criteria may also be used in the construction of the cost function. The optimized treatment plan may be considered as optimally fulfilling the set of clinical goals.

F. Method

Figure 8:
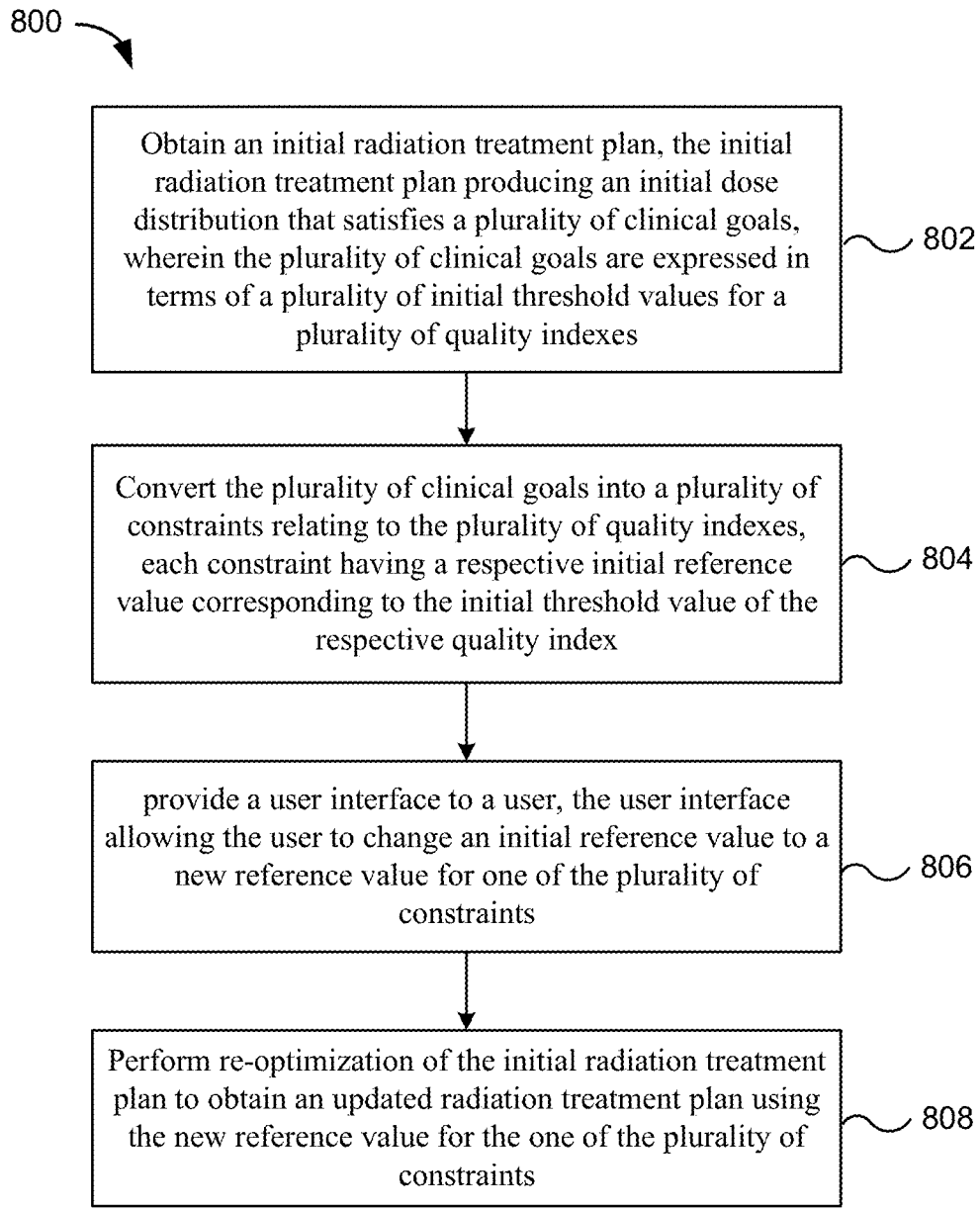
FIG. 8 shows a simplified flowchart illustrating a method for interactively manipulating dose distribution of a radiation treatment plan according to an embodiment of the present invention.

FIG. 8 shows a simplified flowchart illustrating a method 800 for interactively manipulating dose distribution of a radiation treatment plan using an external-beam radiation treatment system according to an embodiment of the present invention.

At 802, an initial radiation treatment plan is obtained. The initial radiation treatment plan produces an initial dose distribution that satisfies a plurality of clinical goals. The plurality of clinical goals are expressed in terms of a plurality of initial threshold values for a plurality of quality indexes. Each quality index relates to a respective statistical quantity of the initial dose distribution.

At 804, the plurality of clinical goals is converted into a plurality of constraints relating to the plurality of quality indexes. Each constraint has a respective initial reference value corresponding to the initial threshold value of the respective quality index. In one embodiment, each respective constraint has a corresponding priority indicating relative importance of the respective constraint among the plurality of constraints.

At 806, a user interface, such as that illustrated in FIG. 6, is provided to a user. The user interface allows the user to change an initial reference value to a new reference value for one of the plurality of constraints. The user can either type in a new numerical value in the user interface or drag a handle in a corresponding DVH curve in the user interface, as discussed above in relation to FIG. 6.

At 808, re-optimization of the initial radiation treatment plan is performed to obtain an updated radiation treatment plan using the new reference value for the one of the plurality of constraints. In one embodiment, the updated radiation treatment plan produces an updated dose distribution that satisfies any constraint that has a higher priority than the one of the plurality of constraints while allowing any constraint that has a lower priority than the one of the plurality of constraints to be violated.

In some embodiments, the updated radiation treatment plan includes a control-point sequence and a multileaf collimator (MLC) leaf sequence to be used by the external-beam radiation treatment system for delivering radiation to a patient. The updated radiation treatment plan may be transmitted to control circuitry of the external-beam radiation treatment system to cause the external-beam radiation treatment system to deliver the radiation to the patient according to the control-point sequence and the multileaf collimator (MLC) leaf sequence of the updated radiation treatment plan.

IV. Radiation Treatment Planning Based on Clinical Goals with Shared Priorities Optimization is often used in IMRT to achieve a treatment plan that best fits a set of clinical goals. Since in general it is not guaranteed that all clinical goals can be fulfilled simultaneously for a particular patient geometry, it may be necessary to prioritize the clinical goals. One approach may be to search a treatment plan that fulfills as many higher priority clinical goals as possible. A prioritized constraint technique, such as the technique of lexicographic ordering, may be used in this approach. The optimization process typically starts with only the highest priority clinical goal. Once a solution meeting that clinical goal is found, the clinical goal is changed to a constraint. Another optimization is then performed using the next highest priority clinical goal as the new optimization objective. This process may be repeated for the remaining clinical goals. If a particular clinical goal cannot be fulfilled, the constraint is set to a value that is acceptable.

A. Using Shared Priorities in Clinical Goal Setting

In some cases, however, it may be difficult to assign a unique priority to each of the clinical goals, or there may be two or more clinical goals that are considered as equally important and yet cannot both be fulfilled at the same time. For instance, consider the example illustrated in FIG. 9. The horizontal axis and the vertical axis are the values of a first quality index $Q_1$ and a second quality index $Q_2$, respectively. For example, the first quality index $Q_1$ may relate to the mean dose Dmean to an OAR (e.g., the spine), and the second quality index $Q_2$ may relate to the maximum dose Dmax to a PTV. A first clinical goal may be expressed in terms of the first quality index $Q_1$ as $Q_1 \leq x_0$, represented by the vertical straight line 910; and a second clinical goal may be expressed in terms of the second quality index $Q_2$ as $Q_2 \leq y_0$, represented by the horizontal straight line 920. The shaded area 930 in the lower left quadrant may represent a region where both the first clinical goal and the second clinical goal are simultaneously satisfied.

In some cases, however, for a particular set of patient geometry and field geometries, an achievable solution may not be found where both the first clinical goal and the second clinical goal can be fulfilled at the same time. For instance, the shaded region 940 represents the region where achievable solutions can be found for a set of given patient geometry and field geometries. In this example, there is no overlap between the shaded region 940 and the shaded region 930, which means that there is no achievable solution that can fulfill both the first clinical goal and the second clinical goal simultaneously.

In such a case, the point 960, where the vertical line 910 and the border line 950 of the region 940 intersects, may represent an achievable solution that fulfills the first clinical goal with a minimum amount of violation of the second clinical goal. Similarly, the point 970, where the horizontal line 920 and the border line 950 of the region 940 intersects, may represent an achievable solution that fulfills the second clinical goal with a minimum amount of violation of the first clinical goal. Thus, if the first clinical goal is considered to be more important than the second clinical goal, then the point 960 may represent an optimal treatment plan. On the other hand, if the second clinical goal is considered to be more important than the first clinical goal, the point 970 may represent an optimal treatment plan. However, in cases where it is not clear whether the first clinical goal is more important than the second clinical goal or vice versa, or the first clinical goal and the second clinical goal are equally important, perhaps neither the point 960 nor the point 970 represents an optimal solution.

For cases where two or more clinical goals share the same priority or it is not clear which clinical goal is more important than the other, embodiments may be designed to seek a solution that minimizes the "distance" to the region where all the clinical goals are met. For instance, in the example illustrated in FIG. 9, a solution represented by the point 980, which is located somewhere between the point 960 and the point 970 along the border line 950 of the region 940. At the point 980, although neither the first clinical goal nor the second clinical goal is met, it may have the closest "distance" to the region 930 where both the first clinical goal and the second clinical goal are met.

B. Specifying Two Sets of Threshold Values for a Set of Clinical Goals

Figure 10:
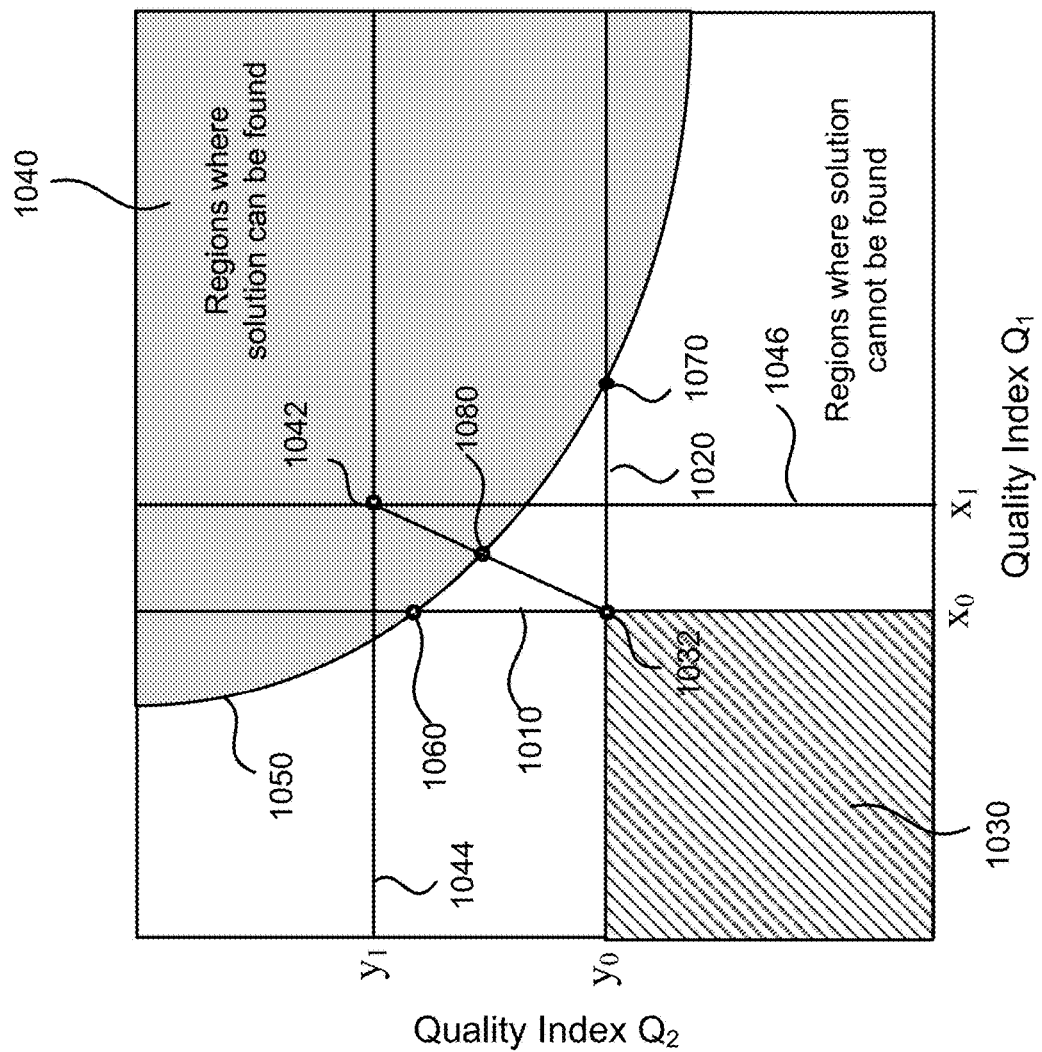
FIG. 10 shows a space spanned by two quality indexes $Q_1$ and $Q_2$, illustrating a method of determining an optimal radiation treatment plan according to an embodiment of the present invention.

Referring to FIG. 10, consider two quality indexes $Q_1$ and $Q_2$, represented by the horizontal axis and the vertical axis, respectively. According to an embodiment of the present invention, a user may specify a first set of threshold values for $Q_1$ and $Q_2$ as follows:

$$Q_1 \le x_0, \text{ and } Q_2 \le y_0.$$

The first set of threshold values $(x_0, y_0)$ may be represented by the point 1032 in FIG. 10. In addition, the user may specify a second set of threshold values for $Q_1$ and $Q_2$ as follows:

$$Q_1 \le x_1, \text{ and } Q_2 \le y_1,$$

where $x_1 > x_0$, and $y_1 > y_0$. The second set of threshold values $(x_1, y_1)$ may be represented by the point 1042 in FIG. 10. Thus, it may be easier to fulfill to the second set of threshold values $(x_1, y_1)$ than the first set of threshold values $(x_0, y_0)$, as the second set of threshold values are higher. The user may assign a higher priority for meeting the second set of threshold values, and a lower priority for meeting the first set of threshold values. For example, the second set of threshold values $(x_1, y_1)$ may represent clinically acceptable threshold values for the quality indexes $Q_1$ and $Q_2$ and thus has to be met, whereas the first set of threshold values $(x_0, y_0)$ may represent desired or preferred threshold values for the quality indexes $Q_1$ and $Q_2$ and can be violated. In one embodiment, the point 1032 resides outside the region 1040 where achievable solutions can be found; and the point 1042 resides inside the region 1040. In other words, the first set of clinical goals $(x_0, y_0)$ cannot be simultaneously fulfilled, while the second set of clinical goals $(x_1, y_1)$ can be simultaneously fulfilled.

An optimizer may construct a cost function designed to reach a solution represented by the point 1080, where the straight line connecting the point 1032 and the point 1042 intersects with the border line 1050 of the region 1040 where solution can be found. The point 1080 may represent an achievable solution that has the minimum "distance" to the region where the first set of threshold values are simultaneously met. As can be seen in FIG. 10, the location of the point 1080 may depend on the values of δx and δy, where δx=$x_1-x_0$, and δy=$y_1-y_0$. In a case where δx=0 and δy is finite, the optimal solution may be represented by the point 1060 where the clinical goal of $x_0$ for $Q_1$ is met. This may be the case where the threshold value $x_0$ for $Q_1$ is so critical such that it has to be met. Conversely, in a case where δy=0 and δx is finite, the optimal solution may be represented by the point 1050 where the threshold value of $y_0$ for $Q_2$ is met. This may be the case where the threshold value $y_0$ for $Q_2$ is so critical such that it has to be met.

For cases where both δx and δy are non-zero, a cost function may be constructed to include a weighted sum of two quadratic terms as:

$$z = w_1 \{\max[0,(Q_1-x_0)]\}^2 + w_2 \{\max[0,(Q_2-y_0)]\}^2, \quad (1)$$

where $$w_1 = \frac{1}{(\delta x)^2}, \text{ and } w_2 = \frac{1}{(\delta y)^2}.$$

Thus, an increase in $Q_1$ in excess of $x_0$, as well as an increase in $Q_2$ in excess of $y_0$, will incur increasing cost, and the relative weights of the first term and the second term are inversely proportional to square of δx and δy, respectively. Therefore, if δx>δy, the second term would have a greater weight than the first term; conversely, if δy>δx, the first term would have a greater weight than the first term. The cost function as expressed in Equation (1) may guide the optimizer toward a solution represented by the point 1080 in FIG. 10, which may be considered as the optimal solution having a minimum weighted "distance" to the region where the desired threshold values of $(x_0, y_0)$ are simultaneously fulfilled. In other embodiments, the terms of the cost function may have forms other than quadratic functions. For example, they may be polynomial functions of an order higher than two, or they may be exponential functions. In some embodiments, the weights $w_1$ and $w_2$ may have forms other than quadratic functions as well. For example, they may be polynomial functions of an order higher than two, or they may be exponential functions. It should be understood that, although the above discussion refers to only two clinical goals expressed in terms of two quality indexes, embodiments can be extended to cases where more than two clinical goals expressed in terms of more than two quality indexes are considered.

C. Specifying Threshold Values as Well as Insignificant Changes for a Set of Quality Indexes In an alternative embodiment, instead of defining a first set of threshold values $(x_0, y_0)$ and a second set of threshold values $(x_1, y_1)$, the user may define a set of desired threshold values $(x_0, y_0)$, and a set of clinically insignificant changes for $Q_1$ and $Q_2$ as (δx, δy). A cost function similar to the cost function expressed in Equation (1) may be used to find an optimal solution.

D. Situations where a Set of Clinical Goals can be Fulfilled Simultaneously

Figure 11:
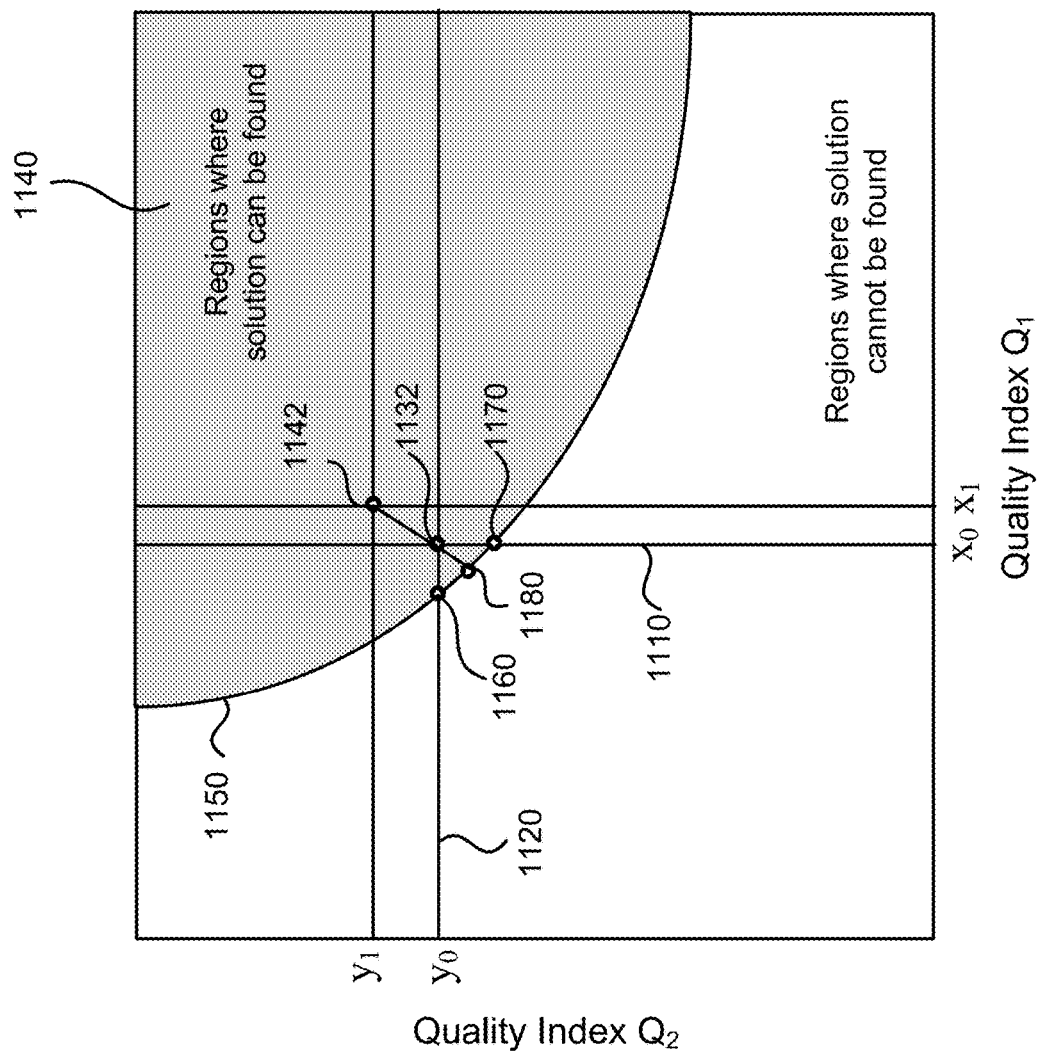
FIG. 11 shows a space spanned by two quality indexes $Q_1$ and $Q_2$, illustrating a method of determining an optimal radiation treatment plan according to another embodiment of the present invention.

The optimization method described above can also be applied to cases where the desired threshold values $(x_0, y_0)$ can be simultaneously fulfilled. For instance, consider the example illustrated in FIG. 11. Here, the point 1132 corresponding to ($x_0$, $y_0$) is located within the region 1140 where solutions can be found. As such, all solutions located within the portion of the region 1140 that is below the horizontal line 1120 and to the left of the vertical line 1110 may satisfy both of the desired threshold values $x_0$ and $y_0$. Therefore, an optimal treatment plan may not be uniquely defined. The solution corresponding to the point 1160 may provide the largest margin to the desired threshold value $x_0$ for the quality index $Q_1$ (i.e., the largest amount by which the actual value of the quality index $Q_1$ falls below the desired threshold value $x_0$), whereas the solution corresponding to the point 1170 may provide the largest margin to the desired threshold value $y_0$ for the quality index $Q_2$.

Instead of seeking a solution that provides the largest margin to the desired threshold value for either of the quality indexes $Q_1$ and $Q_2$, the optimizer may seek a solution that maximizes the margin in terms of the "distance" to the point 1132 having the desired threshold values ($x_0$, $y_0$). Assume that the point 1142 corresponds to the acceptable threshold values ($x_1$, $y_1$). In one embodiment, the optimizer may seek to find a solution represented by the point 1180, where the extension of the straight line connecting the point 1132 and the point 1142 intersects with the border line 1150 of the region 1140, as point 1180 may provide the largest margin in terms of the weighted "distance" to the point 1132.

E. Example User Interface

Figure 12:
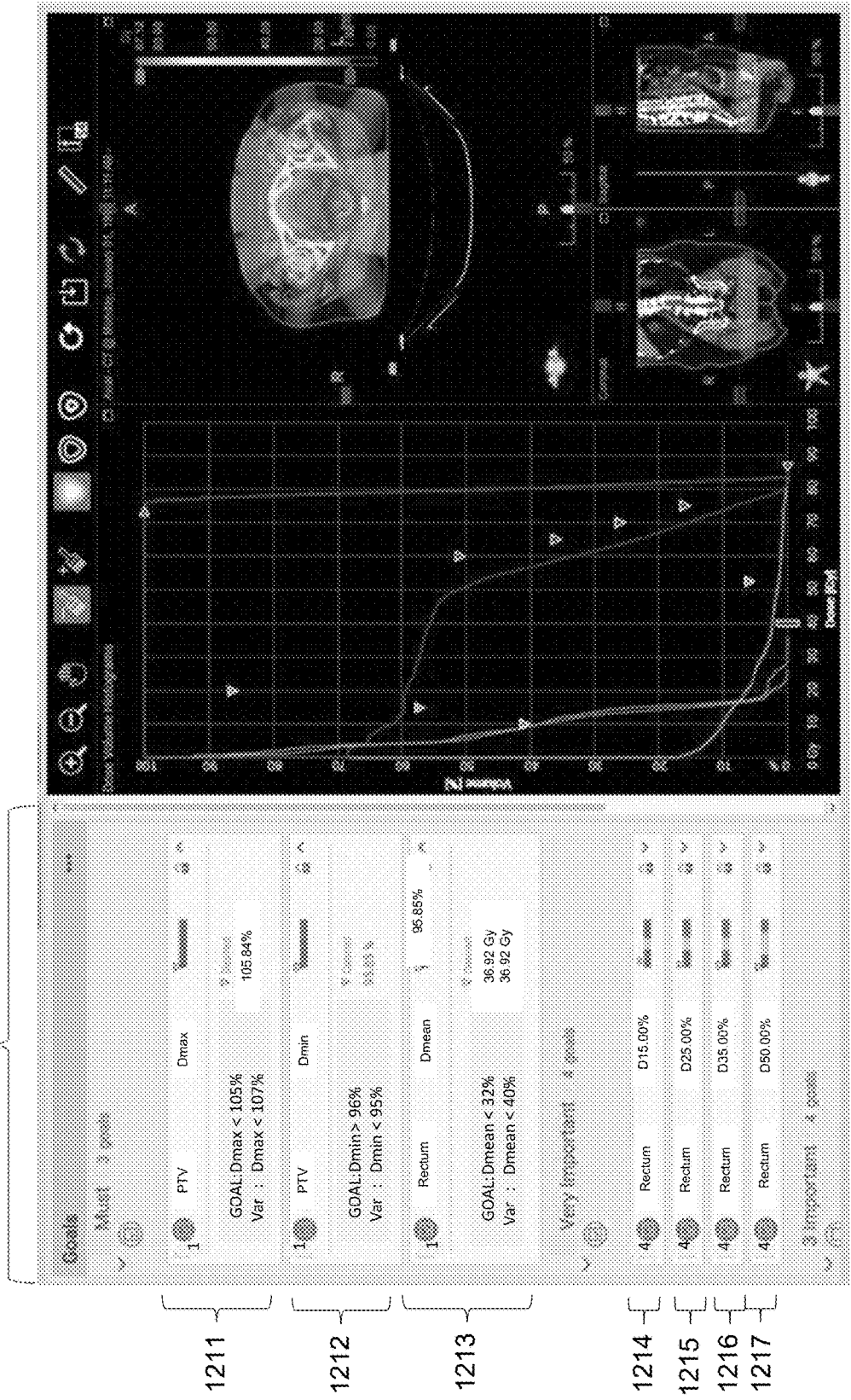
FIG. 12 illustrates an exemplary user interface that may be used in a method of determining an optimal radiation treatment plan according to an embodiment of the present invention.

FIG. 12 illustrates an exemplary user interface that may be used in the optimization process according to an embodiment of the present invention. The section 1210 on the left side of the user interface includes a plurality of fields 1211-1217. Each field corresponds to a clinical goal with regard to a respective quality index. For each clinical goal, a user may specify a first threshold value and a second threshold value for the respective quality index. In some embodiments, the first threshold value may be a preferred value, and the second threshold value may be an acceptable value. For instance, in the example illustrated in FIG. 12, the first threshold value is shown as the "GOAL," and the second threshold value is shown as the "Var." For example, in the first field 1211, the first threshold value for Dmax to the PTV is specified to be 105%, and the second threshold value for Dmax to the PTV is specified to be 107%. In some embodiments, the user may interactively change the first threshold value and/or the second threshold value for each clinical goal during the optimization process. The optimizer may perform optimization of a treatment plan based on the specified threshold values for the clinical goals using the method described above.

F. Method

FIG. 13 shows a simplified flowchart illustrating a method 1300 of determining an optimal radiation treatment plan using an external-beam radiation treatment system according to an embodiment of the present invention.

At 1302, a first clinical goal and a second clinical goal are received via a user interface of a computer system. The first clinical goal includes a first acceptable threshold value and a first desired threshold value for a first quality index. The second clinical goal includes a second acceptable threshold value and a second desired threshold value for a second quality index. In some embodiments, the difference between the first acceptable threshold value and the first desired threshold value may correspond to a clinically insignificant change for the first quality index, and the difference between the second acceptable threshold value and the second desired threshold value may correspond to a clinically insignificant change for the second quality index.

At 1304, a cost function is obtained. The cost function includes a first term with a first weight and a second term with a second weight. The first term is proportional to a value of the first quality index in excess of the first acceptable threshold value, and the second term is proportional to a value of the second quality index in excess of the second acceptable threshold value. The first weight is inversely proportional to a difference between the first desired threshold value and the first acceptable threshold value, and the second weight is inversely proportional to a difference between the second desired threshold value and the second acceptable threshold value.

At 1306, optimization is performed using the cost function to obtain an optimal radiation treatment plan that has an optimal value for the cost function.

In some embodiments, the first term of the cost function is proportional to square of the value of the first quality index in excess of the first acceptable threshold value, and the second term is proportional to square of the value of the second quality index in excess of the second acceptable threshold value. The first weight is inversely proportional to square of the difference between the first desired threshold value and the first acceptable threshold value, and the second weight is inversely proportional to square of the difference between the second desired threshold value and the second acceptable threshold value. For example, the cost function may have the form expressed in Equation (1).

V. Generating a Radiation Treatment Plan Based on Clinical Goals and Trade-Offs Among the Clinical Goals In optimizing a radiation treatment plan, it is often necessary to interpret a set of user defined clinical goals in terms of a cost function. The cost function assigns a single scalar value for each plan as a function of all the "microscopic" degrees of freedom (MDF) in the treatment plan. The MDF can be the set of all fluence pixels in all fields or the set of all free machine parameters needed to deliver the treatment plan. The optimization problem may be then reduced to finding a plan that has the minimum cost function value.

Figure 9:
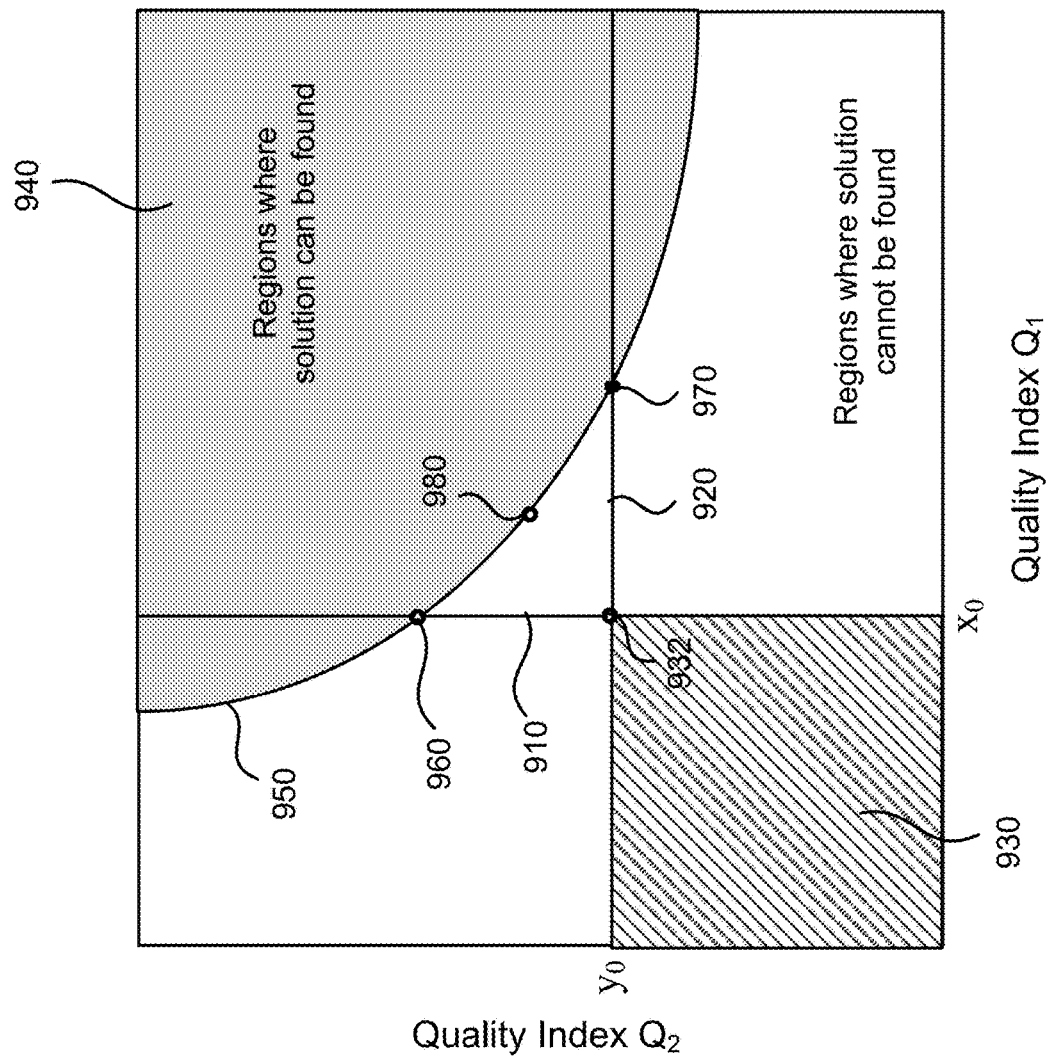
FIG. 9 shows a space spanned by two quality indexes $Q_1$ and $Q_2$, which includes a region where solution can be found and a region where a set of clinical goals with respect to $Q_1$ and $Q_2$ can be simultaneously fulfilled, according to an embodiment of the present invention.

In some cases where more than one clinical goals are provided, it may not be guaranteed that all clinical goals can be fulfilled simultaneously, as described in the previous section in relation to FIG. 9. One approach may be to also specify the relative priorities of the different clinical goals, so as to instruct the optimizer which goal should be fulfilled first. On the other hand, in some cases there may be more than one treatment plans that can satisfy all clinical goals. For instance, in the example illustrated in FIG. 11, any point in the portion of region 1140 below the horizontal straight line 1120 and to the left of the vertical straight line 1110 may represent a solution that satisfies both clinical goals ($x_0$, $y_0$) simultaneously. In such cases, the set of clinical goals ($x_0$, $y_0$) may not uniquely determine an optimal plan, but only reduces the set of achievable plans.

A. Cost Function Based on Clinical Goals

Figure 14:
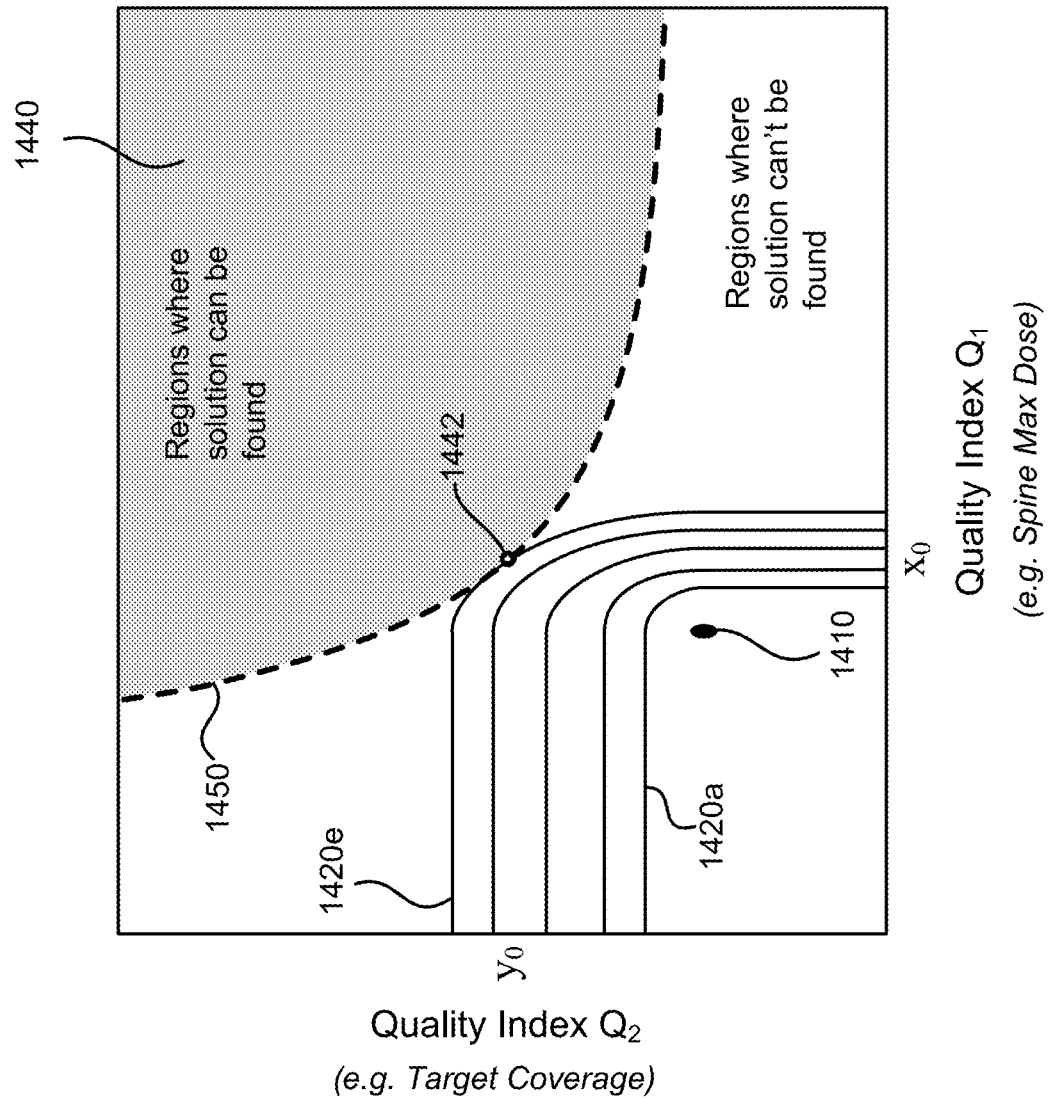
FIG. 14 shows a space spanned by two quality indexes $Q_1$ and $Q_2$, illustrating a method of determining an optimal radiation treatment plan according to an embodiment of the present invention.

Consider a case where two clinical goals are presented in terms of threshold values for two quality indexes $Q_1$ and $Q_2$ as $Q_1 \leq x_0$ and $Q_2 \leq y_0$. One way of constructing a cost function is to include a weighted sum of two quadratic terms as, $$z = w_1\{\max[0,(Q_1-x_0)]\}^2 + w_2\{\max[0,(Q_2-y_0)]\}^2, \quad (2)$$

where $w_1$ and $w_2$ are the weights for the two quadratic terms. Referring to FIG. 14, the point 1410 correspond to the threshold values ($x_0$, $y_0$) and may be referred to as the "objective location." The contour lines 1420a-1420e represent a set of iso-curves of the cost function z. The objective of an optimization may be to minimize the value of the cost function z for a set of patient geometry and field geometries. For instance, in the example illustrated in FIG. 14, the shaded region 1440 represents the region where achievable solutions can be found for a given patient geometry. The point 1442 where the iso-curve 1420e just touches the border line 1450 of the region 1440 may represent an optimal achievable solution that has the lowest possible cost function value.

The constraint location 1410 is usually chosen such that the reference values ($x_0$, $y_0$) are related to but not the same as clinically acceptable threshold values for $Q_1$ and $Q_2$. In other words, the objective location 1410 is usually selected to be outside the region 1440, so that the cost function has a finite gradient and thus can be minimized. Choosing the objective location 1410 usually requires some experience. According to some embodiments, users may set the objective location manually.

B. Trade-Offs Between Clinical Goals

In some cases, however, it may be problematic to use a static cost function that only depends on the threshold values for the clinical goals. In some cases, a physician may not consider a treatment plan that satisfies a set of clinical goals as the best possible plan. For instance, consider the examples illustrated in FIG. 15. The point 1510 is the objective location. Contour lines 1520a-1520g are the iso-curves of a cost function as expressed in Equation (2). Consider a first case where a first feasible solution space for a first patient geometry is defined by the first border curve 1550. In this case, the point 1552, where the iso-curve 1520g of the cost function just touches the first border curve 1550, may represent a potential optimal solution. Now consider a second case where a second feasible solution space for a second patient geometry is defined by the second border curve 1560. Here, the point 1562, where the iso-curve 1520g of the cost function just touches the second border curve 1560, may represent a potential optimal solution. Thus, although the solution corresponding to the point 1552 and the solution corresponding to the point 1562 lie on the same iso-curve and hence have the same cost function value, the two solutions are obviously very different. This illustrates that the same form of cost function may lead to very different solutions depending on the shape of the solution space.

In some cases, a physician may prefer to consider trade-offs between two quality indexes where much can be gained in one quality index without reducing significantly the other. For instance, in the first example illustrated in FIG. 15, the point 1552 lies on a section of the first border curve 1550 where it is substantially horizontal. This means that another solution in the vicinity of the point 1552 along the border curve 1550 may only incur a small change in the value of $Q_2$ but can have a large reduction in the value of $Q_1$. For example, consider the alternative solution represented by the point 1554. Its value of $Q_2$ is only slightly increased from the value of $Q_2$ at the point 1552, yet its value of $Q_1$ is significantly reduced from the value of $Q_1$ at the point 1552. Thus, a physician may prefer the alternative solution represented by the point 1554 over the solution represented by the point 1552, as long as the increase in the value of $Q_2$ is within the clinically insignificant change of $Q_2$.

Figure 15:
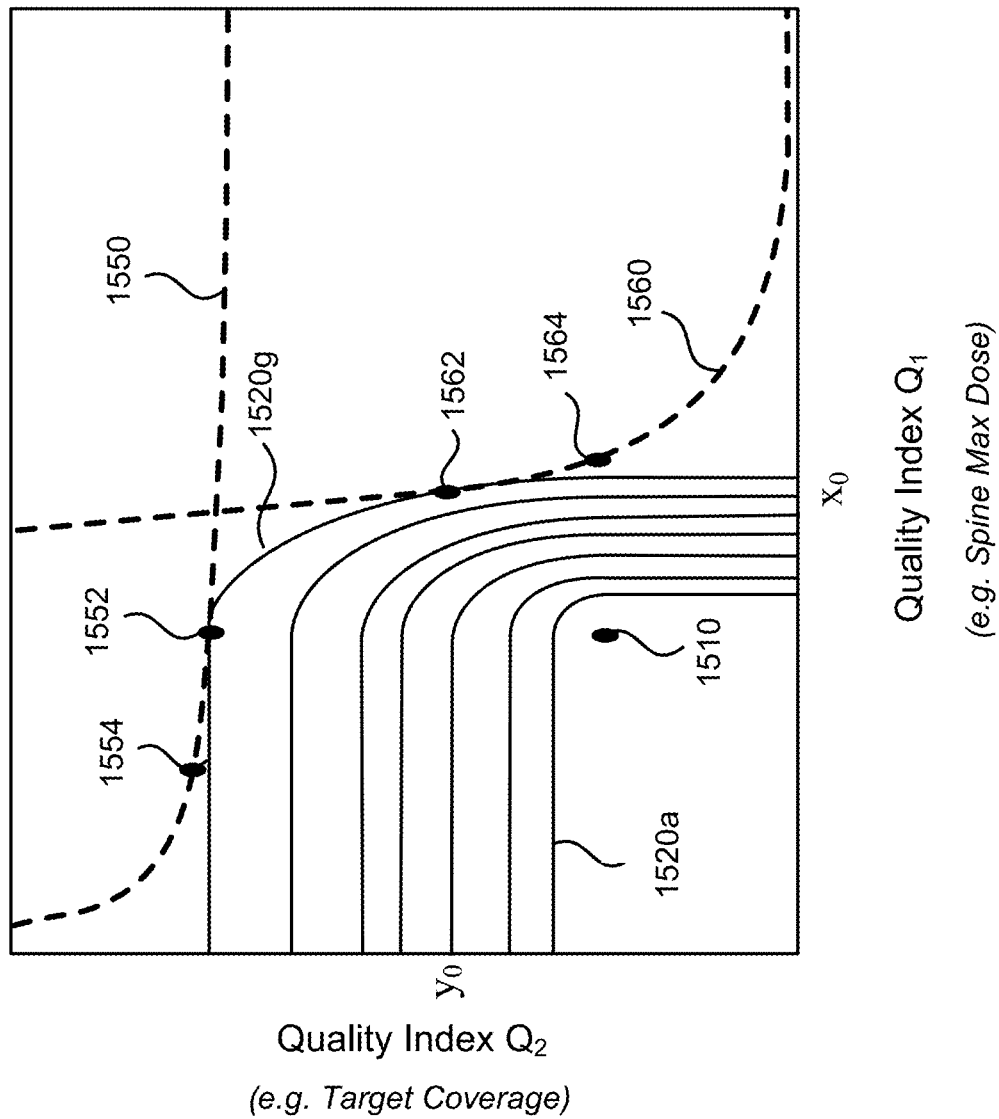
FIG. 15 shows a space spanned by two quality indexes $Q_1$ and $Q_2$, illustrating a method of determining an optimal radiation treatment plan according to another embodiment of the present invention.

Similarly, in the second example illustrated in FIG. 15, the point 1562 lies on a section of the second border curve 1560 where it is substantially vertical. This means that another solution in the vicinity of the point 1562 along the border curve 1560 may only incur a small change in the value of $Q_1$ but can have a large reduction in the value of $Q_2$. For example, consider the alternative solution represented by the point 1564. Its value of $Q_1$ is only slightly increased from the value of $Q_1$ at the point 1562, yet its value of $Q_2$ is significantly reduced from the value of $Q_2$ at the point 1562. Thus, a physician may prefer the alternative solution represented by the point 1564 over the solution represented by the point 1562, as long as the increase in the value of $Q_1$ is within the clinically insignificant change of $Q_1$. In cases where the objective location is far inside the region where the solution can be found, consideration of trade-offs may be even more important, as optimization may be driven by some secondary terms, such as fluence smoothing and monitor unit (MU) count objectives.

C. Cost Function Based on Clinical Goals and Trade-Offs Among Clinical Goals As discussed above with relation to FIG. 15, it may be desirable to construct a cost function that not only takes into account a set of clinical goals, but also possible trade-offs among the set of clinical goals. According to embodiments of the present invention, an optimizer can support clinical goals where the user has specified preferable trade-offs in advance. For example, the user can specify clinically insignificant changes as well as clinically significant changes for each quality indexes. In some embodiments, the cost function can be generated and dynamically altered during optimization so that any solution achieving clinically significant improvement in one quality index while only deteriorating the other quality index by an insignificant amount may be accepted. In one embodiment, the optimizer may change the objective location whenever the cost function gradient in a space spanned by the quality indexes has a much greater component with respect to one quality index compared to the other quality index.

According to an embodiment of the present invention, a cost function may include a term relating to threshold values for the quality indexes, as well as terms relating to user-specified clinically insignificant and clinically significant changes for the quality indexes. For example, consider two clinical goals involving a first quality index $Q_1$ and a second quality index $Q_2$. The optimizer may construct a cost function z that may include the following three terms, $$\sqrt{w_1^2\{\max[0,(Q_1-x_0)]\}^2 + w_2^2\{\max[0,(Q_2-y_0)]\}^2}, \quad (3)$$

$$w_1 \delta x_L \cdot Q_1 + w_2 \delta y_H \cdot Q_2 + ax, \quad (4)$$

$$w_1 \delta x_H \cdot Q_1 + w_2 \delta y_L \cdot Q_2 + bx, \quad (5)$$

where each term presents the cost function in a different region of the ($Q_1$, $Q_2$) plane. The values of $x_0$ and $y_0$ define a constraint location; $\delta x_L$ and $\delta y_L$ are the user-specified clinically insignificant changes in $Q_1$ and $Q_2$, respectively; $\delta x_H$ and $dy_H$ are the user-specified clinically significant changes in $Q_1$ and $Q_2$, respectively; $w_1$ and $w_2$ are relative weights. The region borders and the parameters a and b are selected so that the cost function contours are continuous and smooth. Normally $\delta x_H > \delta x_L$, and $\delta y_H > \delta y_L$. For example, assume that $Q_1$ corresponds to the maximum dose Dmax to an OAR. A user may specify that the clinically insignificant change for $Q_1$ $\delta x_L$ is 0.5 Gy, and the clinically significant change for $Q_1$ $\delta x_H$ is 5 Gy.

In some embodiments, the second term expressed in Equation (4) and the third term expressed in Equation (5) may guide the optimization toward a solution that keeps the quality index gradients within the bounds of $\delta x_L$ and $\delta y_L$, and $\delta x_H$ and $\delta y_H$. For example, referring to FIG. 15, in the case where the border line for the region where the solution can be found is defined by the curve 1550, the new cost function may be designed to have its iso-curves shaped such that it may lead to the solution located at point 1554 instead of 1552, so as to take advantage of the beneficial trade-offs. On the other hand, in the case where the border line for the region where the solution can be found is defined by the curve 1560, the new cost function may be designed to have its iso-curves shaped such that it will lead to the solution located at point 1564 instead of 1562, so as to take advantage of the beneficial trade-offs. It should be understood that, although the above discussion refers to only two quality indexes, the method can be extended to cases where more than two quality indexes are considered.

In some embodiments, instead of specifying clinically significant changes and clinically insignificant changes for the quality indexes, the user may specify desired threshold values as well as acceptable threshold values for the quality indexes. For example, the user may specify the desired threshold values for $Q_1$ and $Q_2$ as $x_0$ and $y_0$, respectively, and specify the acceptable threshold values for $Q_1$ and $Q_2$ as $x_1$ and $y_1$, respectively, where $x_1 > x_0$ and $y_1 > y_0$. The desired threshold values $x_0$ and $y_0$ would be the primary driver for the optimization, and the acceptable threshold values $x_1$ and $y_1$ are used to constrain the optimizer's search for user preferred trade-offs.

D. Cost Function Including Cross Terms Among Clinical Goals

In another embodiment, the optimizer may construct a cost function z that includes the following two terms, $$w_1\{\max[0,(Q_1-x_0)]\}^2 + w_2\{\max[0,(Q_2-y_0)]\}^2, \quad (6)$$

$$w_{12}\max\{0,(Q_1-x_0)\}\max\{0,(Q_2-y_0)\}, \quad (7)$$

where the weights $w_1$, $w_2$, and $w_{12}$ are selected such that certain quality index gradients are preferred. The cross term expressed in Equation (7) may guide the optimizer toward an optimal solution that takes advantages of any beneficial trade-offs.

E. Dynamic Change of Objective Location

According to an embodiment of the present invention, the optimizer may change the objective location whenever the cost function gradient in a space spanned by the quality indexes has a much greater component with respect to one quality index compared to the other quality index. For instance, in the example illustrated in FIG. 15, consider the solution corresponding to the point 1552. Since this point is almost directly above the constraint location 1510, the cost function value at this point has a much greater contribution from the term $w_2 \{\max [0, (Q_2-y_0)]\}^2$ than from the term $w_1 \{\max [0, (Q_1-x_0)]\}^2$. This means that the solution 1552 is located at a position where the gradient of the quality index $Q_1$ is very high, i.e., a small reduction in the value of $Q_2$ can cause large increase in the value of $Q_1$. In one embodiment, upon recognizing such a situation, the optimizer may move the objective location 1510 toward the left, i.e., reducing the value of $x_0$, so that the cost function value may have a greater contribution from the term $w_1\{\max [0, (Q_1-x_0)]\}^2$.

F. Other Embodiments

In some embodiments of the present invention, trade-off information may be deduced from knowledge models. For example, potentially beneficial trade-offs may be deduced automatically from a selected set of existing treatment plans using machine learning algorithms, such as those similar to some current DVH estimation algorithms.

In some other embodiments, similar approaches can be used to restrict the solution space in multi-criteria-optimization (MCO), where the cost function is a vector valued function.

The optimization approaches described above may afford several advantages. For example, in cases where a set of clinical goals does not uniquely determine an optimal plan but only reduces the set of achievable plans, or in cases where not all clinical goals can be satisfied, taking into account information about the acceptable or preferred trade-offs in the optimization can guide the optimizer to the optimal treatment plan.

G. Example User Interface

FIG. 16 illustrates an exemplary user interface that may be used in the optimization process according to an embodiment of the present invention. The section 1610 on the left side of the user interface includes a plurality of fields 1611-1617. Each field corresponds to a clinical goal with regard to a respective quality index. In some embodiments, for each clinical goal, a user may specify a desired threshold value (i.e., the "GOAL"), as well as a clinically "significant change" and a clinically "insignificant change," for the respective quality index. For example, in the first field 1611, the desired threshold value for Dmax to the PTV is specified to be 105%, the clinically significant change is specified to be 1%, and the clinically insignificant change is specified to be 0.1%. The system may optimize a treatment plan based on the user-specified threshold values, as well as clinically significant changes and clinically insignificant changes. In some embodiments, the user may interactively change the desired threshold values, as well as the clinically significant changes and the clinically insignificant changes during the optimization process.

H. Method

FIG. 17 shows a simplified flowchart illustrating a method 1700 of determining an optimal radiation treatment plan using an external-beam radiation treatment system according to an embodiment of the present invention.

At 1702, a first clinical goal and a second clinical goal is received via a user interface of a computer system. The first clinical goal includes a first threshold value for a first quality index relating to a first statistical quantity of a dose distribution. the second clinical goal includes a second threshold value for a second quality index relating to a second statistical quantity of the dose distribution.

At 1704, a first clinically significant change and a first clinically insignificant change for the first quality index are received. Also, a second clinically significant change and a second clinically insignificant change for the second quality index are received.

At 1706, a cost function is obtained. The cost function includes a first term, a second term, and a third term. The first term is proportional to a value of the first quality index in excess of the first threshold value and proportional to a value of the second quality index in excess of the second threshold value. The second term relates to the first clinically insignificant change for the first quality index and to the second clinically significant change for the second quality index. The third term relates to the first clinically significant change for the first quality index and to the second clinically insignificant change for the second quality index. In one embodiment, the first term of the cost function may have the form expressed in Equation (3).

At 1708, optimization is performed using the cost function to obtain an optimal radiation treatment plan that has an optimal value for the cost function.

In some embodiments, the second term of the cost function is proportional to a product of the first clinically insignificant change and the value of the first quality index, and proportional to a product of the second clinically significant change and the value of the second quality index. For example, the second term may have the form expresses in Equation (4). The third term of the cost function is proportional to a product of the first clinically significant change and the value of the first quality index, and proportional to a product of the second clinically insignificant change and the value of the second quality index. For example, the third term may have the form expressed in Equation (5).

VI. Computer System

Figure 18:
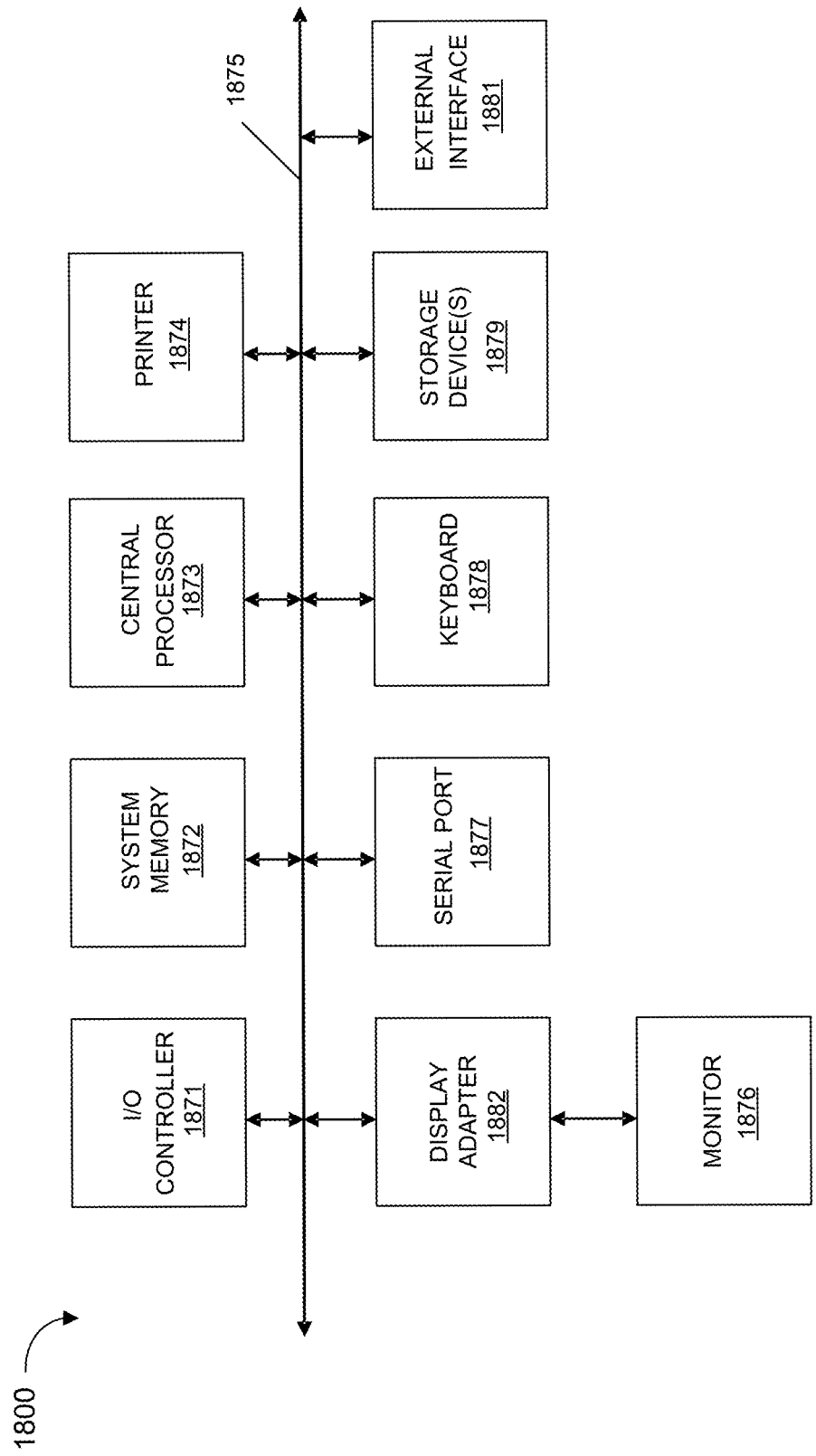
FIG. 18 shows a block diagram of an example computer system usable with system and methods according to embodiments of the present invention.

Any of the computer systems mentioned herein may utilize any suitable number of subsystems. Examples of such subsystems are shown in FIG. 18 in computer system 1800. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 18 are interconnected via a system bus 1875. Additional subsystems such as a printer 1874, keyboard 1878, storage device(s) 1879, monitor 1876, which is coupled to display adapter 1882, and others are shown. Peripherals and input/output (I/O) devices, which couple to I/O controller 1871, can be connected to the computer system by any number of means known in the art, such as serial port 1877. For example, serial port 1877 or external interface 1881 (e.g. Ethernet, Wi-Fi, etc.) can be used to connect computer system 1800 to a wide area network such as the Internet, a mouse input device, or a scanner. The interconnection via system bus 1875 allows the central processor 1873 to communicate with each subsystem and to control the execution of instructions from system memory 1872 or the storage device(s) 1879 (e.g., a fixed disk, such as a hard drive or optical disk), as well as the exchange of information between subsystems. The system memory 1872 and/or the storage device(s) 1879 may embody a computer readable medium. Any of the data mentioned herein can be output from one component to another component and can be output to the user.

A computer system can include a plurality of the same components or subsystems, e.g., connected together by external interface 1881 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

What is claimed is:

1. A computer product comprising a non-transitory computer readable medium storing a plurality of instructions that when executed control a computer system to allow interactive manipulation of dose distribution of a radiation treatment plan using an external-beam radiation treatment system, the instructions comprising:
    obtaining, by the computer system, an initial radiation treatment plan, the initial radiation treatment plan producing an initial dose distribution that satisfies a plurality of clinical goals, wherein the plurality of clinical goals are expressed in terms of a plurality of initial threshold values for a plurality of quality indexes, each respective quality index relating to a respective statistical quantity of the initial dose distribution;
    converting, by the computer system, the plurality of clinical goals into a plurality of constraints relating to the plurality of quality indexes, each constraint having a respective initial reference value corresponding to the initial threshold value of the respective quality index, each respective constraint having a corresponding priority indicating relative importance of the respective constraint among the plurality of constraints;
    providing a user interface to a user, the user interface allowing the user to change an initial reference value to a new reference value for one of the plurality of constraints; and
    performing, by the computer system, re-optimization of the initial radiation treatment plan to obtain an updated radiation treatment plan using the new reference value for the one of the plurality of constraints, the updated radiation treatment plan producing an updated dose distribution, wherein the re-optimization enforces the updated dose distribution to satisfy any constraint that has a priority higher than a priority of the one of the plurality of constraints while allowing any constraint that has a priority lower than the priority of the one of the plurality of constraints to be violated.

2. The computer product of claim 1, wherein the updated radiation treatment plan includes a control-point sequence and a multileaf collimator (MLC) leaf sequence to be used by the external-beam radiation treatment system for delivering radiation to a patient.

3. The computer product of claim 2, wherein the instructions further comprise:
    transmitting the updated radiation treatment plan to control circuitry of the external-beam radiation treatment system to cause the external-beam radiation treatment system to deliver the radiation to the patient according to the control-point sequence and the multileaf collimator (MLC) leaf sequence of the updated radiation treatment plan.

4. The computer product of claim 1, wherein the updated dose distribution satisfies the one of the plurality of constraints having the new reference value.

5. The computer product of claim 1, wherein the updated dose distribution minimizes an amount of violation of each constraint that is violated.

6. The computer product of claim 5, wherein the updated dose distribution corresponds to an achieved reference value for each constraint that is violated, and the instructions further comprise replacing the initial reference value of each constraint that is violated with the achieved reference value.

7. The computer product of claim 1, wherein another one of the plurality of constraints has a same priority as the one of the plurality of constraints, and wherein the updated dose distribution satisfies the another one of the plurality of constraints.

8. The computer product of claim 1, wherein another one of the plurality of constraints has a same priority as the one of the plurality of constraints, and wherein the updated dose distribution is allowed to violate the another one of the plurality of constraints.

9. The computer product of claim 1, wherein the instructions further comprise:
    allowing the user to, at the user interface, create a new constraint corresponding to a new quality index; and
    performing, by the computer system, re-optimization of the updated radiation treatment plan to obtain a second updated radiation treatment plan using the new constraint.

10. The computer product of claim 1, wherein the instructions further comprise:
    allowing the user to, at the user interface, change priorities of one or more of the plurality of constraints; and
    performing, by the computer system, re-optimization of the updated radiation treatment plan to obtain a second updated radiation treatment plan, the second updated radiation treatment plan produces a second updated dose distribution that satisfies as many constraints of higher priorities as possible.

11. A computer product comprising a non-transitory computer readable medium storing a plurality of instructions that when executed control a computer system to determine a radiation treatment plan for delivering radiation to a patient using an external-beam radiation treatment system, the instructions comprising:
    receiving, via a user interface of the computer system, a first clinical goal and a second clinical goal, wherein the first clinical goal includes a first acceptable threshold value and a first desired threshold value for a first quality index relating to a first statistical quantity of a dose distribution, and the second clinical goal includes a second acceptable threshold value and a second desired threshold value for a second quality index relating to a second statistical quantity of the dose distribution;
    obtaining, by the computer system, a cost function including a first term with a first weight and a second term with a second weight, wherein the first term is proportional to a value of the first quality index in excess of the first acceptable threshold value, and the second term is proportional to a value of the second quality index in excess of the second acceptable threshold value, and wherein the first weight is inversely proportional to a difference between the first desired threshold value and the first acceptable threshold value, and the second weight is inversely proportional to a difference between the second desired threshold value and the second acceptable threshold value; and performing, by the computer system, optimization using the cost function to obtain an optimal radiation treatment plan having an optimal value for the cost function.

12. The computer product of claim 11, wherein the optimal radiation treatment plan includes a control-point sequence and a multileaf collimator (MLC) leaf sequence to be used by the external-beam radiation treatment system for delivering radiation to a patient.

13. The computer product of claim 12, wherein the instructions further comprise:

transmitting the optimal radiation treatment plan to control circuitry of the external-beam radiation treatment system to cause the external-beam radiation treatment system to deliver the radiation to the patient according to the control-point sequence and the multileaf collimator (MLC) leaf sequence of the optimal radiation treatment plan.

14. The computer product of claim 11, wherein the first term of the cost function is proportional to square of the value of the first quality index in excess of the first acceptable threshold value, and the second term is proportional to square of the value of the second quality index in excess of the second acceptable threshold value.

15. The computer product of claim 14, wherein the first weight is inversely proportional to square of the difference between the first desired threshold value and the first acceptable threshold value, and the second weight is inversely proportional to square of the difference between the second desired threshold value and the second acceptable threshold value.

16. The computer product of claim 11, wherein the difference between the first desired threshold value and the first acceptable threshold value is a clinically insignificant change for the first quality index, and the difference between the second desired threshold value and the second acceptable threshold value is a clinically insignificant change for the second quality index.

17. A computer product comprising a non-transitory computer readable medium storing a plurality of instructions that when executed control a computer system to determine a radiation treatment plan for delivering radiation to a patient using an external-beam radiation treatment system, the instructions comprising:

receiving, via a user interface of the computer system, a first clinical goal and a second clinical goal, wherein the first clinical goal includes a first threshold value for a first quality index relating to a first statistical quantity of a dose distribution, and the second clinical goal includes a second threshold value for a second quality index relating to a second statistical quantity of the dose distribution;

receiving, by the computer system, a first clinically significant change and a first clinically insignificant change for the first quality index, and a second clinically significant change and a second clinically insignificant change for the second quality index;

obtaining, by the computer system, a cost function including a first term, a second term, and a third term, wherein the first term is proportional to a value of the first quality index in excess of the first threshold value and proportional to a value of the second quality index in excess of the second threshold value, the second term relates to the first clinically insignificant change for the first quality index and to the second clinically significant change for the second quality index, and the third term relates to the first clinically significant change for the first quality index and to the second clinically insignificant change for the second quality index; and performing, by the computer system, optimization using the cost function to obtain an optimal radiation treatment plan having an optimal value for the cost function.

18. The computer product of claim 17, wherein the optimal radiation treatment plan includes a control-point sequence and a multileaf collimator (MLC) leaf sequence to be used by the external-beam radiation treatment system for delivering radiation to a patient.

19. The computer product of claim 17, wherein:

the second term of the cost function is proportional to a product of the first clinically insignificant change and the value of the first quality index, and proportional to a product of the second clinically significant change and the value of the second quality index; and the third term of the cost function is proportional to a product of the first clinically significant change and the value of the first quality index, and proportional to a product of the second clinically insignificant change and the value of the second quality index.

20. The computer product of claim 17, wherein the first clinically significant change and the first clinically insignificant change for the first quality index, and the second clinically significant change and the second clinically insignificant change for the second quality index are determined based on a selected set of existing radiation treatment plans.

* * * * *